(12) United States Patent
Staniforth et al.

(10) Patent No.: US 9,797,612 B2
(45) Date of Patent: *Oct. 24, 2017

(54) FAN ASSEMBLY

(71) Applicant: Dyson Technology Limited, Wiltshire (GB)

(72) Inventors: Mark Joseph Staniforth, Bristol (GB); Daniel James Beavis, Wakefield (GB); Jude Paul Pullen, London (GB); Paul Richard Riggs, Oxford (GB)

(73) Assignee: Dyson Technology Limited, Malmesbury, Wiltshire (GB)

( * ) Notice: Subject to any disclaimer, the term of this patent is extended or adjusted under 35 U.S.C. 154(b) by 526 days.

This patent is subject to a terminal disclaimer.

(21) Appl. No.: 14/166,152

(22) Filed: Jan. 28, 2014

(65) Prior Publication Data
US 2014/0210115 A1 Jul. 31, 2014

(30) Foreign Application Priority Data
Jan. 29, 2013 (GB) .................................. 1301573.0

(51) Int. Cl.
*F24F 6/14* (2006.01)
*F24F 13/26* (2006.01)
(Continued)

(52) U.S. Cl.
CPC .................. *F24F 6/14* (2013.01); *F24F 6/12* (2013.01); *F24F 13/26* (2013.01); *A61L 2/10* (2013.01);
(Continued)

(58) Field of Classification Search
CPC ........ F24F 6/14; F24F 2003/1667; A61L 2/10
See application file for complete search history.

(56) References Cited

U.S. PATENT DOCUMENTS

| 284,962 A | 9/1883 | Huston |
|---|---|---|
| 1,357,261 A | 11/1920 | Svoboda |

(Continued)

FOREIGN PATENT DOCUMENTS

| BE | 560119 | 8/1957 |
|---|---|---|
| CA | 1055344 | 5/1979 |

(Continued)

OTHER PUBLICATIONS

Translation of Iwao JP 2003-161473 published Jun. 6, 2003 translated by Schreiber Translations, Inc. on Feb. 2015.*

(Continued)

*Primary Examiner* — Amber R Orlando
*Assistant Examiner* — Stephen Hobson
(74) *Attorney, Agent, or Firm* — Morrison & Foerster LLP

(57) ABSTRACT

Humidifying apparatus includes a chamber, and a water tank for supplying water to the chamber. A baffle located within the chamber divides the chamber into an inlet section and an outlet section, and guides water received from the water tank along the inlet section to the outlet section. An air flow is conveyed over water stored in the outlet section of the chamber and is emitted from the apparatus. Water within both the inlet section and the outlet section of the chamber is irradiated with ultraviolet radiation. The water within the outlet section is atomized by a transducer to humidify the air flow.

18 Claims, 25 Drawing Sheets

(51) Int. Cl.
  *F24F 6/12*     (2006.01)
  *F24F 3/16*     (2006.01)
  *A61L 2/10*     (2006.01)

(52) U.S. Cl.
  CPC ..... *F24F 2003/1667* (2013.01); *Y02B 30/545* (2013.01); *Y02B 30/80* (2013.01)

(56) References Cited

U.S. PATENT DOCUMENTS

| | | | |
|---|---|---|---|
| 1,767,060 A | 6/1930 | Ferguson | |
| 1,896,869 A | 2/1933 | Larsh | |
| 2,014,185 A | 9/1935 | Martin | |
| 2,035,733 A | 3/1936 | Wall | |
| 2,071,266 A | 2/1937 | Schmidt | |
| D103,476 S | 3/1937 | Weber | |
| 2,115,883 A | 5/1938 | Sher | |
| D115,344 S | 6/1939 | Chapman | |
| 2,210,458 A | 8/1940 | Keilholtz | |
| 2,258,961 A | 10/1941 | Saathoff | |
| 2,295,502 A | 9/1942 | Lamb | |
| 2,336,295 A | 12/1943 | Reimuller | |
| 2,363,839 A | 11/1944 | Demuth | |
| 2,433,795 A | 12/1947 | Stokes | |
| 2,473,325 A | 6/1949 | Aufiero | |
| 2,476,002 A | 7/1949 | Stalker | |
| 2,488,467 A | 11/1949 | De Lisio | |
| 2,510,132 A | 6/1950 | Morrison | |
| 2,544,379 A | 3/1951 | Davenport | |
| 2,547,448 A | 4/1951 | Demuth | |
| 2,583,374 A | 1/1952 | Hoffman | |
| 2,620,127 A | 12/1952 | Radcliffe | |
| 2,711,682 A | 6/1955 | Drechsel | |
| 2,755,106 A | 7/1956 | Brennan et al. | |
| 2,765,977 A | 10/1956 | Morrison | |
| 2,808,198 A | 10/1957 | Morrison | |
| 2,813,673 A | 11/1957 | Smith | |
| 2,830,779 A | 4/1958 | Wentling | |
| 2,838,229 A | 6/1958 | Belanger | |
| 2,922,277 A | 1/1960 | Bertin | |
| 2,922,570 A | 1/1960 | Allen | |
| 3,004,403 A | 10/1961 | Laporte | |
| 3,047,208 A | 7/1962 | Coanda | |
| 3,270,655 A | 9/1966 | Guirl et al. | |
| D206,973 S | 2/1967 | De Lisio | |
| 3,503,138 A | 3/1970 | Fuchs et al. | |
| 3,518,776 A | 7/1970 | Wolff et al. | |
| 3,724,092 A | 4/1973 | McCleerey | |
| 3,729,934 A | 5/1973 | Denning et al. | |
| 3,743,186 A | 7/1973 | Mocarski | |
| 3,795,367 A | 3/1974 | Mocarski | |
| 3,872,916 A | 3/1975 | Beck | |
| 3,875,745 A | 4/1975 | Franklin | |
| 3,885,891 A | 5/1975 | Throndson | |
| 3,943,329 A | 3/1976 | Hlavac | |
| 4,037,991 A | 7/1977 | Taylor | |
| 4,046,492 A | 9/1977 | Inglis | |
| 4,061,188 A | 12/1977 | Beck | |
| 4,073,613 A | 2/1978 | Desty | |
| 4,090,814 A | 5/1978 | Teodorescu et al. | |
| 4,113,416 A | 9/1978 | Kataoka et al. | |
| 4,136,735 A | 1/1979 | Beck et al. | |
| 4,173,995 A | 11/1979 | Beck | |
| 4,180,130 A | 12/1979 | Beck et al. | |
| 4,184,417 A | 1/1980 | Chancellor | |
| 4,184,541 A | 1/1980 | Beck et al. | |
| 4,192,461 A | 3/1980 | Arborg | |
| 4,264,837 A | 4/1981 | Gaboriaud | |
| 4,332,529 A | 6/1982 | Alperin | |
| 4,336,017 A | 6/1982 | Desty | |
| 4,342,204 A | 8/1982 | Melikian et al. | |
| 4,448,354 A | 5/1984 | Reznick et al. | |
| 4,568,243 A | 2/1986 | Schubert et al. | |
| 4,630,475 A | 12/1986 | Mizoguchi | |
| 4,643,351 A | 2/1987 | Fukamachi et al. | |
| 4,703,152 A | 10/1987 | Shih-Chin | |
| 4,716,946 A | 1/1988 | Grigoletto | |
| 4,718,870 A | 1/1988 | Watts | |
| 4,732,539 A | 3/1988 | Shin-Chin | |
| 4,734,017 A | 3/1988 | Levin | |
| 4,790,133 A | 12/1988 | Stuart | |
| 4,850,804 A | 7/1989 | Huang | |
| 4,878,620 A | 11/1989 | Tarleton | |
| 4,893,990 A | 1/1990 | Tomohiro et al. | |
| 4,978,281 A | 12/1990 | Conger | |
| 5,061,405 A | 10/1991 | Stanek et al. | |
| D325,435 S | 4/1992 | Coup et al. | |
| 5,110,266 A | 5/1992 | Toyoshima et al. | |
| 5,168,722 A | 12/1992 | Brock | |
| 5,176,856 A | 1/1993 | Takahashi et al. | |
| 5,188,508 A | 2/1993 | Scott et al. | |
| D343,231 S | 1/1994 | Lim | |
| 5,296,769 A | 3/1994 | Havens et al. | |
| D346,017 S | 4/1994 | Lim | |
| 5,310,313 A | 5/1994 | Chen | |
| 5,317,815 A | 6/1994 | Hwang | |
| 5,338,495 A | 8/1994 | Steiner et al. | |
| 5,402,938 A | 4/1995 | Sweeney | |
| 5,407,324 A | 4/1995 | Starnes, Jr. et al. | |
| 5,425,902 A | 6/1995 | Miller et al. | |
| 5,435,489 A | 7/1995 | Jenkins et al. | |
| 5,483,616 A | 1/1996 | Chiu et al. | |
| 5,518,370 A | 5/1996 | Wang et al. | |
| D374,712 S | 10/1996 | Jane et al. | |
| 5,609,473 A | 3/1997 | Litvin | |
| 5,645,769 A | 7/1997 | Tamaru et al. | |
| 5,649,370 A | 7/1997 | Russo | |
| D382,951 S | 8/1997 | Deines et al. | |
| 5,671,321 A | 9/1997 | Bagnuolo | |
| 5,677,982 A | 10/1997 | Levine et al. | |
| 5,706,985 A | 1/1998 | Feer | |
| 5,735,683 A | 4/1998 | Muschelknautz | |
| 5,762,034 A | 6/1998 | Foss | |
| 5,762,661 A | 6/1998 | Kleinberger et al. | |
| 5,783,117 A | 7/1998 | Byassee et al. | |
| 5,794,306 A | 8/1998 | Firdaus | |
| D398,983 S | 9/1998 | Keller et al. | |
| 5,841,080 A | 11/1998 | Iida et al. | |
| 5,843,344 A | 12/1998 | Junket et al. | |
| 5,859,952 A * | 1/1999 | Levine | F24F 1/02 239/102.1 |
| 5,862,037 A | 1/1999 | Behl | |
| 5,868,197 A | 2/1999 | Potier | |
| 5,881,685 A | 3/1999 | Foss et al. | |
| 5,922,247 A | 7/1999 | Shoham et al. | |
| D415,271 S | 10/1999 | Feer | |
| 6,015,274 A | 1/2000 | Bias et al. | |
| D423,663 S | 4/2000 | Rossman et al. | |
| 6,073,881 A | 6/2000 | Chen | |
| D429,808 S | 8/2000 | Krauss et al. | |
| 6,123,618 A | 9/2000 | Day | |
| 6,155,782 A | 12/2000 | Hsu | |
| D435,899 S | 1/2001 | Melwani | |
| 6,200,155 B1 | 3/2001 | Chudkosky et al. | |
| 6,254,337 B1 | 7/2001 | Arnold | |
| 6,269,549 B1 | 8/2001 | Carlucci et al. | |
| 6,278,248 B1 | 8/2001 | Hong et al. | |
| 6,282,746 B1 | 9/2001 | Schleeter | |
| 6,293,121 B1 | 9/2001 | Labrador | |
| 6,321,034 B2 | 11/2001 | Jones-Lawlor et al. | |
| 6,386,845 B1 | 5/2002 | Bedard | |
| 6,480,672 B1 | 11/2002 | Rosenzweig et al. | |
| 6,599,088 B2 | 7/2003 | Stagg | |
| 6,604,694 B1 | 8/2003 | Kordas et al. | |
| D483,851 S | 12/2003 | Fok | |
| D485,895 S | 1/2004 | Melwani | |
| D486,903 S | 2/2004 | Chiang | |
| 6,715,739 B2 | 4/2004 | Mulvaney et al. | |
| 6,789,787 B2 | 9/2004 | Stutts | |
| 6,791,056 B2 | 9/2004 | VanOtteren et al. | |
| 6,830,433 B2 | 12/2004 | Birdsell et al. | |
| 6,845,971 B2 | 1/2005 | Bachert | |
| D512,772 S | 12/2005 | Lee | |
| D513,067 S | 12/2005 | Blateri | |
| 7,059,826 B2 | 6/2006 | Lasko | |

(56) References Cited

U.S. PATENT DOCUMENTS

| | | |
|---|---|---|
| 7,088,913 B1 | 8/2006 | Verhoorn et al. |
| 7,147,336 B1 | 12/2006 | Chou |
| D539,414 S | 3/2007 | Russak et al. |
| 7,192,258 B2 | 3/2007 | Kuo et al. |
| 7,198,473 B2 | 4/2007 | Stickland et al. |
| D544,078 S | 6/2007 | Geringer |
| 7,362,964 B2 | 4/2008 | Wang |
| 7,412,781 B2 | 8/2008 | Mattinger et al. |
| 7,478,993 B2 | 1/2009 | Hong et al. |
| 7,540,474 B1 | 6/2009 | Huang et al. |
| D595,835 S | 7/2009 | Fu |
| D598,532 S | 8/2009 | Dyson et al. |
| D602,143 S | 10/2009 | Gammack et al. |
| D602,144 S | 10/2009 | Dyson et al. |
| D605,748 S | 12/2009 | Gammack et al. |
| 7,660,110 B2 | 2/2010 | Vinson et al. |
| 7,664,377 B2 | 2/2010 | Liao |
| D614,280 S | 4/2010 | Dyson et al. |
| 7,731,050 B2 | 6/2010 | Parks et al. |
| 7,775,848 B1 | 8/2010 | Auerbach |
| 7,806,388 B2 | 10/2010 | Junkel et al. |
| 7,841,045 B2 | 11/2010 | Shaanan et al. |
| D633,997 S | 3/2011 | Hideharu et al. |
| D633,999 S | 3/2011 | Hideharu et al. |
| 7,931,449 B2 | 4/2011 | Fitton et al. |
| D638,114 S | 5/2011 | Li et al. |
| D643,098 S | 8/2011 | Wallace et al. |
| 8,002,520 B2 | 8/2011 | Dawson et al. |
| D644,726 S | 9/2011 | Hideharu et al. |
| D645,133 S | 9/2011 | Hideharu |
| D646,373 S | 10/2011 | Liebson et al. |
| 8,092,166 B2 | 1/2012 | Nicolas et al. |
| 8,113,490 B2 | 2/2012 | Chen |
| 8,152,495 B2 | 4/2012 | Boggess, Jr. et al. |
| 8,246,317 B2 | 8/2012 | Gammack |
| D669,164 S | 10/2012 | Hsu |
| 8,308,445 B2 | 11/2012 | Gammack et al. |
| D672,023 S | 12/2012 | Wallace et al. |
| D672,024 S | 12/2012 | Fitton et al. |
| 8,348,629 B2 | 1/2013 | Fitton et al. |
| 8,356,804 B2 | 1/2013 | Fitton et al. |
| D676,536 S | 2/2013 | Roach et al. |
| D678,993 S | 3/2013 | Kung-Hua |
| 8,403,640 B2 | 3/2013 | Gammack et al. |
| 8,408,869 B2 | 4/2013 | Hutton et al. |
| D681,793 S | 5/2013 | Li |
| D684,249 S | 6/2013 | Herbst |
| 8,454,322 B2 | 6/2013 | Gammack et al. |
| 8,469,660 B2 | 6/2013 | Dyson et al. |
| 8,529,226 B2 | 9/2013 | Li |
| 8,544,826 B2 | 10/2013 | Ediger et al. |
| D698,018 S | 1/2014 | Choi |
| D700,959 S | 3/2014 | Sickinger et al. |
| 8,684,687 B2 | 4/2014 | Dyson et al. |
| D705,415 S | 5/2014 | Lo |
| 8,721,286 B2 | 5/2014 | Gammack et al. |
| 8,721,307 B2 | 5/2014 | Li |
| 8,764,412 B2 | 7/2014 | Gammack et al. |
| 8,783,663 B2 | 7/2014 | Fitton et al. |
| 8,784,071 B2 | 7/2014 | Gammack |
| 2001/0017212 A1 | 8/2001 | Hirano |
| 2002/0104972 A1 | 8/2002 | Guzorek |
| 2002/0106547 A1 | 8/2002 | Sugawara et al. |
| 2002/0190400 A1* | 12/2002 | Bachert ............... B01F 3/0407 261/81 |
| 2003/0059307 A1 | 3/2003 | Moreno et al. |
| 2003/0064677 A1 | 4/2003 | Terrell et al. |
| 2003/0164367 A1 | 9/2003 | Bucher et al. |
| 2003/0171093 A1 | 9/2003 | Gumucio Del Pozo |
| 2003/0190183 A1 | 10/2003 | Hsing |
| 2003/0230477 A1 | 12/2003 | Fink et al. |
| 2004/0022631 A1 | 2/2004 | Birdsell et al. |
| 2004/0049842 A1 | 3/2004 | Prehodka |
| 2004/0106370 A1 | 6/2004 | Honda et al. |
| 2004/0149881 A1 | 8/2004 | Allen |
| 2005/0031448 A1 | 2/2005 | Lasko et al. |
| 2005/0053465 A1 | 3/2005 | Roach et al. |
| 2005/0069407 A1 | 3/2005 | Winkler et al. |
| 2005/0128698 A1 | 6/2005 | Huang |
| 2005/0163670 A1 | 7/2005 | Alleyne et al. |
| 2005/0173997 A1 | 8/2005 | Schmid et al. |
| 2005/0194167 A1 | 9/2005 | Kiyota et al. |
| 2005/0258554 A1 | 11/2005 | Bachert |
| 2005/0281672 A1 | 12/2005 | Parker et al. |
| 2006/0172682 A1 | 8/2006 | Orr et al. |
| 2006/0199515 A1 | 9/2006 | Lasko et al. |
| 2006/0263073 A1 | 11/2006 | Clarke et al. |
| 2006/0279927 A1 | 12/2006 | Strohm |
| 2007/0009354 A1 | 1/2007 | Zahuranec |
| 2007/0035189 A1 | 2/2007 | Matsumoto |
| 2007/0041857 A1 | 2/2007 | Fleig |
| 2007/0065280 A1 | 3/2007 | Fok |
| 2007/0166160 A1 | 7/2007 | Russak et al. |
| 2007/0176502 A1 | 8/2007 | Kasai et al. |
| 2007/0224044 A1 | 9/2007 | Hong et al. |
| 2007/0237500 A1 | 10/2007 | Wang |
| 2007/0269323 A1 | 11/2007 | Zhou et al. |
| 2008/0020698 A1 | 1/2008 | Spaggiari |
| 2008/0124060 A1 | 5/2008 | Gao |
| 2008/0152482 A1 | 6/2008 | Patel |
| 2008/0166224 A1 | 7/2008 | Giffin |
| 2008/0286130 A1 | 11/2008 | Purvines |
| 2008/0314250 A1 | 12/2008 | Cowie et al. |
| 2009/0026850 A1 | 1/2009 | Fu |
| 2009/0032130 A1 | 2/2009 | Dumas et al. |
| 2009/0039805 A1 | 2/2009 | Tang |
| 2009/0060710 A1 | 3/2009 | Gammack et al. |
| 2009/0060711 A1 | 3/2009 | Gammack et al. |
| 2009/0078120 A1 | 3/2009 | Kummer et al. |
| 2009/0120925 A1 | 5/2009 | Lasko |
| 2009/0191054 A1 | 7/2009 | Winkler |
| 2009/0214341 A1 | 8/2009 | Craig |
| 2009/0301482 A1 | 12/2009 | Burton et al. |
| 2010/0133707 A1 | 6/2010 | Huang |
| 2010/0150699 A1 | 6/2010 | Nicolas et al. |
| 2010/0162011 A1 | 6/2010 | Min |
| 2010/0171465 A1 | 7/2010 | Seal et al. |
| 2010/0225012 A1* | 9/2010 | Fitton ............... F24F 1/01 261/116 |
| 2010/0226749 A1 | 9/2010 | Gammack et al. |
| 2010/0226750 A1 | 9/2010 | Gammack |
| 2010/0226751 A1 | 9/2010 | Gammack et al. |
| 2010/0226752 A1 | 9/2010 | Gammack et al. |
| 2010/0226753 A1 | 9/2010 | Dyson et al. |
| 2010/0226754 A1 | 9/2010 | Hutton et al. |
| 2010/0226758 A1 | 9/2010 | Cookson et al. |
| 2010/0226763 A1 | 9/2010 | Gammack et al. |
| 2010/0226764 A1 | 9/2010 | Gammack et al. |
| 2010/0226769 A1 | 9/2010 | Helps |
| 2010/0226771 A1 | 9/2010 | Crawford et al. |
| 2010/0226787 A1 | 9/2010 | Gammack et al. |
| 2010/0226797 A1 | 9/2010 | Fitton et al. |
| 2010/0226801 A1 | 9/2010 | Gammack |
| 2010/0254800 A1 | 10/2010 | Fitton et al. |
| 2011/0058935 A1 | 3/2011 | Gammack et al. |
| 2011/0080724 A1 | 4/2011 | Jörgensen |
| 2011/0110805 A1 | 5/2011 | Gammack et al. |
| 2011/0164959 A1 | 7/2011 | Fitton et al. |
| 2011/0223014 A1 | 9/2011 | Crawford et al. |
| 2011/0223015 A1 | 9/2011 | Gammack et al. |
| 2011/0236228 A1 | 9/2011 | Fitton et al. |
| 2011/0248096 A1 | 10/2011 | Lin et al. |
| 2012/0031509 A1 | 2/2012 | Wallace et al. |
| 2012/0033952 A1 | 2/2012 | Wallace et al. |
| 2012/0034108 A1 | 2/2012 | Wallace et al. |
| 2012/0039705 A1 | 2/2012 | Gammack |
| 2012/0045315 A1 | 2/2012 | Gammack |
| 2012/0045316 A1 | 2/2012 | Gammack |
| 2012/0051884 A1 | 3/2012 | Junkel et al. |
| 2012/0057959 A1 | 3/2012 | Hodgson et al. |
| 2012/0082561 A1 | 4/2012 | Gammack et al. |
| 2012/0093629 A1 | 4/2012 | Fitton et al. |
| 2012/0093630 A1 | 4/2012 | Fitton et al. |
| 2012/0107096 A1 | 5/2012 | Yang et al. |

(56) References Cited

U.S. PATENT DOCUMENTS

| | | | |
|---|---|---|---|
| 2012/0114513 A1 | 5/2012 | Simmonds et al. | |
| 2012/0230658 A1 | 9/2012 | Fitton et al. | |
| 2012/0308375 A1 | 12/2012 | Gammack | |
| 2012/0318393 A1 | 12/2012 | Tsen | |
| 2012/0319311 A1* | 12/2012 | Nutter | F24F 6/02 261/72.1 |
| 2013/0011252 A1 | 1/2013 | Crawford et al. | |
| 2013/0026664 A1 | 1/2013 | Staniforth et al. | |
| 2013/0028763 A1 | 1/2013 | Staniforth et al. | |
| 2013/0028766 A1 | 1/2013 | Staniforth et al. | |
| 2013/0077292 A1 | 3/2013 | Zimmerman | |
| 2013/0129490 A1 | 5/2013 | Dos Reis et al. | |
| 2013/0142676 A1 | 6/2013 | Zou | |
| 2013/0143481 A1 | 6/2013 | Kagawa et al. | |
| 2013/0161842 A1 | 6/2013 | Fitton et al. | |
| 2013/0175711 A1 | 7/2013 | Nutter et al. | |
| 2013/0199372 A1 | 8/2013 | Nock et al. | |
| 2013/0234346 A1 | 9/2013 | Staniforth et al. | |
| 2013/0234347 A1 | 9/2013 | Staniforth et al. | |
| 2013/0249122 A1 | 9/2013 | Staniforth et al. | |
| 2013/0249124 A1 | 9/2013 | Staniforth et al. | |
| 2013/0249126 A1 | 9/2013 | Staniforth et al. | |
| 2013/0272858 A1 | 10/2013 | Stickney et al. | |
| 2013/0280051 A1 | 10/2013 | Nicolas et al. | |
| 2013/0280061 A1 | 10/2013 | Stickney | |
| 2013/0280096 A1 | 10/2013 | Gammack et al. | |
| 2013/0309065 A1 | 11/2013 | Johnson et al. | |
| 2013/0309080 A1 | 11/2013 | Johnson et al. | |
| 2013/0320574 A1 | 12/2013 | Sickinger et al. | |
| 2013/0323100 A1 | 12/2013 | Poulton et al. | |
| 2013/0336771 A1 | 12/2013 | Dyson et al. | |
| 2014/0017069 A1 | 1/2014 | Peters | |
| 2014/0077398 A1 | 3/2014 | Staniforth et al. | |
| 2014/0079566 A1 | 3/2014 | Gammack et al. | |
| 2014/0084492 A1 | 3/2014 | Staniforth et al. | |
| 2014/0210114 A1 | 7/2014 | Staniforth et al. | |
| 2014/0255173 A1 | 9/2014 | Poulton et al. | |
| 2014/0255217 A1 | 9/2014 | Li | |
| 2015/0084214 A1 | 3/2015 | Wilson et al. | |
| 2016/0032927 A1 | 2/2016 | Johnson et al. | |
| 2016/0032941 A1 | 2/2016 | Beavis et al. | |
| 2016/0033148 A1 | 2/2016 | Darvill | |
| 2016/0033150 A1 | 2/2016 | Staniforth et al. | |

FOREIGN PATENT DOCUMENTS

| | | |
|---|---|---|
| CA | 2155482 | 9/1996 |
| CH | 346643 | 5/1960 |
| CN | 2085866 | 10/1991 |
| CN | 2111392 | 7/1992 |
| CN | 2549372 | 5/2003 |
| CN | 1437300 | 8/2003 |
| CN | 1446116 | 10/2003 |
| CN | 2650005 | 10/2004 |
| CN | 2713643 | 7/2005 |
| CN | 1680727 | 10/2005 |
| CN | 1724950 | 1/2006 |
| CN | 2833197 | 11/2006 |
| CN | 201011346 | 1/2008 |
| CN | 201147215 | 11/2008 |
| CN | 201180678 | 1/2009 |
| CN | 201221477 | 4/2009 |
| CN | 101424279 | 5/2009 |
| CN | 101451754 | 6/2009 |
| CN | 201281416 | 7/2009 |
| CN | 201349269 | 11/2009 |
| CN | 101684828 | 3/2010 |
| CN | 201486901 | 5/2010 |
| CN | 101726100 | 6/2010 |
| CN | 101749288 | 6/2010 |
| CN | 201502549 | 6/2010 |
| CN | 201507461 | 6/2010 |
| CN | 201518985 | 7/2010 |
| CN | 101825096 | 9/2010 |
| CN | 101825101 | 9/2010 |
| CN | 101825102 | 9/2010 |
| CN | 101825103 | 9/2010 |
| CN | 101825104 | 9/2010 |
| CN | 101825324 | 9/2010 |
| CN | 201568337 | 9/2010 |
| CN | 101858355 | 10/2010 |
| CN | 101936310 | 1/2011 |
| CN | 201696365 | 1/2011 |
| CN | 201696366 | 1/2011 |
| CN | 201739199 | 2/2011 |
| CN | 101984299 | 3/2011 |
| CN | 101985948 | 3/2011 |
| CN | 201763705 | 3/2011 |
| CN | 201763706 | 3/2011 |
| CN | 201770513 | 3/2011 |
| CN | 201771875 | 3/2011 |
| CN | 201779080 | 3/2011 |
| CN | 201786777 | 4/2011 |
| CN | 201786778 | 4/2011 |
| CN | 201802648 | 4/2011 |
| CN | 301539668 | 5/2011 |
| CN | 102095236 | 6/2011 |
| CN | 201858204 | 6/2011 |
| CN | 201874898 | 6/2011 |
| CN | 201874901 | 6/2011 |
| CN | 201917047 | 8/2011 |
| CN | 102251973 | 11/2011 |
| CN | 102287357 | 12/2011 |
| CN | 202101355 | 1/2012 |
| CN | 102367813 | 3/2012 |
| CN | 202267207 | 6/2012 |
| CN | 301949285 | 6/2012 |
| CN | 202431623 | 9/2012 |
| CN | 102900654 | 1/2013 |
| CN | 103697556 | 4/2014 |
| DE | 1 291 090 | 3/1969 |
| DE | 24 51 557 | 5/1976 |
| DE | 27 48 724 | 5/1978 |
| DE | 3644567 | 7/1988 |
| DE | 195 10 397 | 9/1996 |
| DE | 197 12 228 | 10/1998 |
| DE | 100 00 400 | 3/2001 |
| DE | 10041805 | 6/2002 |
| DE | 10 2009 039 783 | 4/2010 |
| DE | 10 2009 007 037 | 8/2010 |
| EP | 0 044 494 | 1/1982 |
| EP | 0186581 | 7/1986 |
| EP | 0 459 812 | 12/1991 |
| EP | 0 784 947 | 7/1997 |
| EP | 0 846 868 | 6/1998 |
| EP | 1 094 224 | 4/2001 |
| EP | 1 138 954 | 10/2001 |
| EP | 1 357 296 | 10/2003 |
| EP | 1 779 745 | 5/2007 |
| EP | 1 939 456 | 7/2008 |
| EP | 1 980 432 | 10/2008 |
| EP | 2 000 675 | 12/2008 |
| EP | 2191142 | 6/2010 |
| EP | 2 230 467 | 9/2010 |
| EP | 2 414 738 | 2/2012 |
| EP | 2 578 889 | 4/2013 |
| FR | 1033034 | 7/1953 |
| FR | 1119439 | 6/1956 |
| FR | 1.387.334 | 1/1965 |
| FR | 2 375 471 | 7/1978 |
| FR | 2 534 983 | 4/1984 |
| FR | 2 640 857 | 6/1990 |
| FR | 2 658 593 | 8/1991 |
| FR | 2794195 | 12/2000 |
| FR | 2 874 409 | 2/2006 |
| FR | 2 906 980 | 4/2008 |
| FR | 2928706 | 9/2009 |
| GB | 22235 | 6/1914 |
| GB | 383498 | 11/1932 |
| GB | 593828 | 10/1947 |
| GB | 601222 | 4/1948 |
| GB | 633273 | 12/1949 |
| GB | 641622 | 8/1950 |

(56) References Cited

FOREIGN PATENT DOCUMENTS

| | | |
|---|---|---|
| GB | 661747 | 11/1951 |
| GB | 861749 | 2/1961 |
| GB | 863 124 | 3/1961 |
| GB | 1067956 | 5/1967 |
| GB | 1 262 131 | 2/1972 |
| GB | 1 265 341 | 3/1972 |
| GB | 1 278 606 | 6/1972 |
| GB | 1 304 560 | 1/1973 |
| GB | 1 403 188 | 8/1975 |
| GB | 1 434 226 | 5/1976 |
| GB | 1 501 473 | 2/1978 |
| GB | 2 094 400 | 9/1982 |
| GB | 2 107 787 | 5/1983 |
| GB | 2 111 125 | 6/1983 |
| GB | 2 178 256 | 2/1987 |
| GB | 2 185 531 | 7/1987 |
| GB | 2 185 533 | 7/1987 |
| GB | 2 218 196 | 11/1989 |
| GB | 2 236 804 | 4/1991 |
| GB | 2 240 268 | 7/1991 |
| GB | 2 242 935 | 10/1991 |
| GB | 2 285 504 | 7/1995 |
| GB | 2 289 087 | 11/1995 |
| GB | 2383277 | 6/2003 |
| GB | 2 428 569 | 2/2007 |
| GB | 2 452 593 | 3/2009 |
| GB | 2452490 | 3/2009 |
| GB | 2463698 | 3/2010 |
| GB | 2464736 | 4/2010 |
| GB | 2466058 | 6/2010 |
| GB | 2468312 | 9/2010 |
| GB | 2468313 | 9/2010 |
| GB | 2468315 | 9/2010 |
| GB | 2468317 | 9/2010 |
| GB | 2468319 | 9/2010 |
| GB | 2468320 | 9/2010 |
| GB | 2468323 | 9/2010 |
| GB | 2468328 | 9/2010 |
| GB | 2468329 | 9/2010 |
| GB | 2468331 | 9/2010 |
| GB | 2468369 | 9/2010 |
| GB | 2468498 | 9/2010 |
| GB | 2473037 | 3/2011 |
| GB | 2479760 | 10/2011 |
| GB | 2482547 | 2/2012 |
| GB | 2484671 | 4/2012 |
| GB | 2484695 | 4/2012 |
| GB | 2484761 | 4/2012 |
| GB | 2493231 | 1/2013 |
| GB | 2493505 | 2/2013 |
| GB | 2493507 | 2/2013 |
| GB | 2499041 | 8/2013 |
| GB | 2500005 | 9/2013 |
| GB | 2500010 | 9/2013 |
| GB | 2500011 | 9/2013 |
| GB | 2500012 | 9/2013 |
| GB | 2504415 | 1/2014 |
| JP | 31-13055 | 8/1956 |
| JP | 35-4369 | 3/1960 |
| JP | 39-7297 | 3/1964 |
| JP | 47-21718 | 10/1972 |
| JP | 49-43764 | 4/1974 |
| JP | 49-150403 | 12/1974 |
| JP | 50-92046 | 8/1975 |
| JP | 51-7258 | 1/1976 |
| JP | 52-121045 | 9/1977 |
| JP | 53-60100 | 5/1978 |
| JP | 56-167897 | 12/1981 |
| JP | 57-71000 | 5/1982 |
| JP | 57-157097 | 9/1982 |
| JP | 61-31830 | 2/1986 |
| JP | 61-116093 | 6/1986 |
| JP | 61-280787 | 12/1986 |
| JP | 62-98099 | 5/1987 |
| JP | 62-223494 | 10/1987 |
| JP | 63-36794 | 3/1988 |
| JP | 63-179198 | 7/1988 |
| JP | 63-198933 | 12/1988 |
| JP | 63-306340 | 12/1988 |
| JP | 64-21300 | 2/1989 |
| JP | 64-58955 | 3/1989 |
| JP | 64-83884 | 3/1989 |
| JP | 1-138399 | 5/1989 |
| JP | 1-224598 | 9/1989 |
| JP | 2-146294 | 6/1990 |
| JP | 2-104872 | 8/1990 |
| JP | 2-218890 | 8/1990 |
| JP | 2-248690 | 10/1990 |
| JP | 3-52515 | 5/1991 |
| JP | 3-267598 | 11/1991 |
| JP | 3-286775 | 12/1991 |
| JP | 4-43895 | 2/1992 |
| JP | 4-366330 | 12/1992 |
| JP | 5-99386 | 4/1993 |
| JP | 5-157093 | 6/1993 |
| JP | 5-164089 | 6/1993 |
| JP | 5-263786 | 10/1993 |
| JP | 6-74190 | 3/1994 |
| JP | 6-86898 | 3/1994 |
| JP | 6-147188 | 5/1994 |
| JP | 6-257591 | 9/1994 |
| JP | 6-280800 | 10/1994 |
| JP | 6-336113 | 12/1994 |
| JP | 7-111174 | 4/1995 |
| JP | 7-190443 | 7/1995 |
| JP | 8-21400 | 1/1996 |
| JP | 8-72525 | 3/1996 |
| JP | 8-313019 | 11/1996 |
| JP | 9-100800 | 4/1997 |
| JP | 9-178083 | 7/1997 |
| JP | 9-287600 | 11/1997 |
| JP | 11-83094 | 3/1999 |
| JP | 11-502586 | 3/1999 |
| JP | 11-227866 | 8/1999 |
| JP | 2000-55419 | 2/2000 |
| JP | 2000-116179 | 4/2000 |
| JP | 2000-201723 | 7/2000 |
| JP | 2001-17358 | 1/2001 |
| JP | 2002-21797 | 1/2002 |
| JP | 2002-138829 | 5/2002 |
| JP | 2002-213388 | 7/2002 |
| JP | 2003-4265 | 1/2003 |
| JP | 2003-161473 | 6/2003 |
| JP | 2003-329273 | 11/2003 |
| JP | 2004-8275 | 1/2004 |
| JP | 2004-208935 | 7/2004 |
| JP | 2004-216221 | 8/2004 |
| JP | 2005-201507 | 7/2005 |
| JP | 2005-307985 | 11/2005 |
| JP | 2006-3042 | 1/2006 |
| JP | 2006-89096 | 4/2006 |
| JP | 2006-189221 | 7/2006 |
| JP | 3124510 | 8/2006 |
| JP | 3127331 | 11/2006 |
| JP | 2007-51826 | 3/2007 |
| JP | 2007-138763 | 6/2007 |
| JP | 2007-138789 | 6/2007 |
| JP | 2008-39316 | 2/2008 |
| JP | 2008-100204 | 5/2008 |
| JP | 2008-107037 | 5/2008 |
| JP | 3144127 | 8/2008 |
| JP | 3146538 | 10/2008 |
| JP | 2008-292078 | 12/2008 |
| JP | 2008-294243 | 12/2008 |
| JP | 2009-44568 | 2/2009 |
| JP | 2009-62986 | 3/2009 |
| JP | D1371413 | 10/2009 |
| JP | 2009-275925 | 11/2009 |
| JP | D1376284 | 12/2009 |
| JP | 2010-46411 | 3/2010 |
| JP | 2010-59845 | 3/2010 |
| JP | 2010-131259 | 6/2010 |
| JP | 2010-203760 | 9/2010 |
| JP | 2010-203764 | 9/2010 |

(56) References Cited

FOREIGN PATENT DOCUMENTS

| | | |
|---|---|---|
| JP | 3168517 | 6/2011 |
| JP | 2011-183204 | 9/2011 |
| JP | 2012-31806 | 2/2012 |
| JP | 2012-149842 | 8/2012 |
| JP | 2012-154527 | 8/2012 |
| JP | 2013-508667 | 3/2013 |
| JP | 2013-185821 | 9/2013 |
| KR | 1999-002660 | 1/1999 |
| KR | 10-2005-0102317 | 10/2005 |
| KR | 2007-0007997 | 1/2007 |
| KR | 20-0448319 | 3/2010 |
| KR | 10-2010-0055611 | 5/2010 |
| KR | 10-0985378 | 9/2010 |
| KR | 10-2011-0096588 | 8/2011 |
| TW | 517825 | 1/2003 |
| TW | 589932 | 6/2004 |
| TW | M394383 | 12/2010 |
| TW | M399027 | 3/2011 |
| TW | M399207 | 3/2011 |
| TW | M407299 | 7/2011 |
| WO | WO-90/13478 | 11/1990 |
| WO | WO-95/06822 | 3/1995 |
| WO | WO-02/073096 | 9/2002 |
| WO | WO-03/058795 | 7/2003 |
| WO | WO-03/069931 | 8/2003 |
| WO | WO-2005/050026 | 6/2005 |
| WO | WO-2005/057091 | 6/2005 |
| WO | WO-2006/008021 | 1/2006 |
| WO | WO-2006/012526 | 2/2006 |
| WO | WO-2007/024955 | 3/2007 |
| WO | WO-2007/048205 | 5/2007 |
| WO | WO-2008/014641 | 2/2008 |
| WO | WO-2008/024569 | 2/2008 |
| WO | WO-2008/139491 | 11/2008 |
| WO | WO-2009/030879 | 3/2009 |
| WO | WO-2009/030881 | 3/2009 |
| WO | WO-2010/100449 | 9/2010 |
| WO | WO-2010/100451 | 9/2010 |
| WO | WO-2010/100452 | 9/2010 |
| WO | WO-2010/100453 | 9/2010 |
| WO | WO-2010/100462 | 9/2010 |
| WO | WO-2011/050041 | 4/2011 |
| WO | WO-2011/147318 | 12/2011 |
| WO | WO-2012/006882 | 1/2012 |
| WO | WO-2012/033517 | 3/2012 |
| WO | WO-2012/052737 | 4/2012 |
| WO | WO-2013/014419 | 1/2013 |
| WO | WO-2013/132218 | 9/2013 |
| WO | WO-2013/132222 | 9/2013 |

OTHER PUBLICATIONS

Li et al., U.S. Office Action dated Oct. 25, 2013, directed to U.S. Appl. No. 13/686,480; 17 pages.
Gammack et al., U.S. Office Action dated Apr. 24, 2014, directed to U.S. Appl. No. 12/716,740; 16 pages.
International Search Report and Written Opinion dated May 9, 2014, directed to International Application No. PCT/GB2014/050022; 8 pages.
Staniforth et al., U.S. Office Action dated Sep. 18, 2014, directed to U.S. Appl. No. 13/559,142; 18 pages.
Staniforth et al., U.S. Office Action dated Mar. 17, 2015, directed to U.S. Appl. No. 13/785,787; 18 pages.
Staniforth et al., U.S. Office Action dated Feb. 27, 2015, directed to U.S. Appl. No. 13/786,014; 7 pages.
Dyson et al., U.S. Office Action dated Apr. 27, 2015, directed to U.S. Appl. No. 29/460,994; 6 pages.
Dyson et al., U.S. Office Action dated Apr. 24, 2015, directed to U.S. Appl. No. 29/460,990; 6 pages.
Dyson et al., U.S. Office Action dated Apr. 10, 2015, directed to U.S. Appl. No. 29/460,989; 7 pages.
Staniforth et al., U.S. Office Action dated Jun. 4, 2015, directed to U.S. Appl. No. 13/784,430; 17 pages.
Dyson et al., U.S. Office Action dated May 28, 2015, directed to U.S. Appl. No. 29/460,993; 9 pages.
Search Report dated Jun. 26, 2013, directed to GB Application No. 1301573.0; 1 page.
Reba, I. (1966). "Applications of the Coanda Effect," *Scientific American* 214:84-92.
Third Party Submission Under 37 CFR 1.99 filed Jun. 2, 2011, directed towards U.S. Appl. No. 12/203,698; 3 pages.
Gammack, P. et al., U.S. Office Action dated Dec. 9, 2010, directed to U.S. Appl. No. 12/203,698; 10 pages.
Gammack, P. et al., U.S. Office Action dated Jun. 21, 2011, directed to U.S. Appl. No. 12/203,698; 11 pages.
Gammack et al., U.S. Office Action dated Sep. 17, 2012, directed to U.S. Appl. No. 13/114,707; 12 pages.
Gammack, P. et al., U.S. Office Action dated Dec. 10, 2010, directed to U.S. Appl. No. 12/230,613; 12 pages.
Gammack, P. et al., U.S. Office Action dated May 13, 2011, directed to U.S. Appl. No. 12/230,613; 13 pages.
Gammack, P. et al., U.S. Office Action dated Sep. 7, 2011, directed to U.S. Appl. No. 12/230,613; 15 pages.
Gammack, P. et al., U.S. Office Action dated Jun. 8, 2012, directed to U.S. Appl. No. 12/230,613; 15 pages.
Gammack et al., U.S. Office Action dated Aug. 20, 2012, directed to U.S. Appl. No. 12/945,558; 15 pages.
Gammack et al., U.S. Office Action dated Feb. 28, 2013, directed to U.S. Appl. No. 12/945,558; 16 pages.
Gammack et al., U.S. Office Action dated Jun. 12, 2013, directed towards U.S. Appl. No. 12/945,558; 20 pages.
Fitton et al., U.S. Office Action dated Nov. 30, 2010 directed to U.S. Appl. No. 12/560,232; 9 pages.
Nicolas, F. et al., U.S. Office Action dated Mar. 7, 2011, directed to U.S. Appl. No. 12/622,844; 10 pages.
Nicolas, F. et al., U.S. Office Action dated Sep. 8, 2011, directed to U.S. Appl. No. 12/622,844; 11 pages.
Helps, D. F. et al., U.S. Office Action dated Feb. 15, 2013, directed to U.S. Appl. No. 12/716,694; 12 pages.
Gammack, P. et al., U.S. Office Action dated Dec. 9, 2010, directed to U.S. Appl. No. 12/716,781; 17 pages.
Gammack, P. et al., U.S. Office Action dated Jun. 24, 2011, directed to U.S. Appl. No. 12/716,781; 19 pages.
Gammack et al. U.S. Office Action dated May 29, 2013, directed to U.S. Appl. No. 13/588,666; 11 pages.
Gammack et al., U.S. Office Action dated Sep. 27, 2013, directed to U.S. Appl. No. 13/588,666; 10 pages.
Gammack et al., U.S. Office Action dated Mar. 14, 2013, directed to U.S. Appl. No. 12/716,740; 15 pages.
Gammack et al., U.S. Office Action dated Sep. 6, 2013, directed to U.S. Appl. No. 12/716,740; 15 pages.
Gammack, P. et al., U.S. Office Action dated Feb. 14, 2013, directed to U.S. Appl. No. 12/716,515; 21 pages.
Gammack, P. et al., U.S. Office Action dated Aug. 19, 2013, directed to U.S. Appl. No. 12/716,515; 20 pages.
Gammack, P. et al., U.S. Office Action dated Feb. 10, 2014, directed to U.S. Appl. No. 12/716,515; 21 pages.
Fitton et al., U.S. Office Action dated Mar. 30, 2012, directed to U.S. Appl. No. 12/716,707; 7 pages.
Fitton et al., U.S. Office Action dated Dec. 31, 2013, directed to U.S. Appl. No. 13/718,693; 8 pages.
Gammack, P. et al. U.S. Office Action dated Oct. 18, 2012, directed to U.S. Appl. No. 12/917,247; 11 pages.
Wallace et al., U.S. Office Action dated Jun. 7, 2013, directed towards U.S. Appl. No. 13/192,223; 30 pages.
Wallace et al., U.S. Office Action dated Oct. 23, 2013, directed to U.S. Appl. No. 13/192,223; 18 pages.
Gammack, P. et al., U.S. Office Action dated Apr. 12, 2011, directed to U.S. Appl. No. 12/716,749; 8 pages.
Gammack, P. et al., U.S. Office Action dated Sep. 1, 2011, directed to U.S. Appl. No. 12/716,749; 9 pages.
Gammack, P. et al., U.S. Office Action dated Jun. 25, 2012, directed to U.S. Appl. No. 12/716,749; 11 pages.
Gammack, P. et al., U.S. Office Action dated May 24, 2011, directed to U.S. Appl. No. 12/716,613; 9 pages.

(56) References Cited

OTHER PUBLICATIONS

Fitton, et al., U.S. Office Action dated Mar. 8, 2011, directed to U.S. Appl. No. 12/716,780; 12 pages.
Fitton, et al., U.S. Office Action dated Sep. 6, 2011, directed to U.S. Appl. No. 12/716,780; 16 pages.
Staniforth et al., U.S. Office Action dated May 25, 2016, directed to U.S. Appl. No. 13/786,313; 19 pages.
Staniforth et al., U.S. Office Action dated Jun. 28, 2016, directed to U.S. Appl. No. 13/785,787; 16 pages.
Staniforth et al., U.S. Office Action dated Aug. 19, 2016, directed to U.S. Appl. No. 13/784,430; 20 pages.
Staniforth et al., U.S. Office Action dated Mar. 11, 2016, directed to U.S. Appl. No. 13/785,954; 16 pages.
Staniforth et al., U.S. Office Action dated Mar. 1, 2016, directed to U.S. Appl. No. 13/786,226; 19 pages.
Staniforth et al., U.S. Office Action dated Mar. 1, 2016, directed to U.S. Appl. No. 13/786,082; 19 pages.
Staniforth et al., U.S. Office Action dated Mar. 30, 2016, directed to U.S. Appl. No. 14/166,472; 47 pages.
Staniforth et al., U.S. Office Action dated Sep. 11, 2015, directed to U.S. Appl. No. 13/785,787; 16 pages.
Staniforth et al., U.S. Office Action dated Sep. 30, 2015, directed to U.S. Appl. No. 13/786,014; 8 pages.
Staniforth et al., U.S. Office Action dated Oct. 15, 2015, directed to U.S. Appl. No. 13/786,313; 18 pages.
Staniforth et al., U.S. Office Action dated Feb. 2, 2016, directed to U.S. Appl. No. 13/784,430; 19 pages.
Staniforth et al., U.S. Office Action dated Sep. 21, 2015, directed to U.S. Appl. No. 13/785,954; 16 pages.
Staniforth et al., U.S. Office Action dated Sep. 25, 2015, directed to U.S. Appl. No. 13/786,226; 20 pages.
Staniforth et al., U.S. Office Action dated Aug. 27, 2015, directed to U.S. Appl. No. 13/786,082; 20 pages.
Fitton et al., U.S. Office Action dated Jun. 13, 2014, directed to U.S. Appl. No. 13/274,998; 11 pages.
Fitton et al., U.S. Office Action dated Jun. 13, 2014, directed to U.S. Appl. No. 13/275,034; 10 pages.
Gammack et al., U.S. Office Action dated Sep. 3, 2014, directed to U.S. Appl. No. 13/861,891; 7 pages.
Dos Reis et al., U.S. Office Action dated Sep. 23, 2014, directed to U.S. Appl. No. 29/466,240; 9 pages.
Dos Reis et al., U.S. Office Action dated Sep. 24, 2014, directed to U.S. Appl. No. 29/466,229; 9 pages.
Dos Reis et al., U.S. Office Action dated Sep. 19, 2014, directed to U.S. Appl. No. 29/466,190; 9 pages.
Mcpherson et al., U.S. Office Action dated Sep. 19, 2014, directed to U.S. Appl. No. 29/466,094; 8 pages.
Mcpherson et al., U.S. Office Action dated Sep. 19, 2014, directed to U.S. Appl. No. 29/466,241; 8 pages.
Mcpherson et al., U.S. Office Action dated Sep. 19, 2014, directed to U.S. Appl. No. 29/466,253; 7 pages.
Dyson et al., U.S. Office Action dated Sep. 12, 2014, directed to U.S. Appl. No. 29/480,896; 10 pages.
Dyson et al., U.S. Office Action dated Sep. 12, 2014, directed to U.S. Appl. No. 29/480,915; 9 pages.
Poulton et al., U.S. Office Action dated Sep. 12, 2014, directed to U.S. Appl. No. 29/480,919; 10 pages.
Deniss. (Sep. 9, 2010) "iFan, The Chinese Clone of the Dyson Air Multiplier," located at <http://chinitech.com/en/chinese-clones/ifan-le-clone-chinois-du-dyson-air-multiplier> visited on Aug. 29, 2014. (6 pages).
Amee. (Mar. 29, 2012) "Breeze Right Bladeless Fan Up to 41% Off," located at <http://madamedeals.com/breeze-right-bladeless-fan-up-to-41-off/> visited on Sep. 3, 2014. (2 pages).
Questel. (Jun. 11, 2014) "Designs-Questel" located at <http://sobjprd.questel.fr/export/QPTUJ214/pdf2/19f053ea-a60f-4c58-9232-c458147a9adf-224304.pdf/> visited on Sep. 4, 2014. (67 pages).
Amazon. "Pisenic Bladeless Fan 16 Inches with Remote Control, Bladeless Fan Air Conditioner 110v, Air Multiplier Table Fans, Green," located at <http://www.amazon.com/Pisenic-Bladeless-Fan-16-Conditioner/dp/B007VCI78M%3FSubscription-id%3DAKIAJYLII7AAJMX7ETAA%26tag%3Dtk78-20%26linkCode%3Dxm2%26camp%3D2025%26creative%-3D165953%26creativeASIN%3DB007VCI78M#cm_cr_dpwidget> visited on Sep. 2, 2014. (4 pages).
Steiner, L., (May 14, 2013) "Dyson Fan Heater Review: Cozy Up to Dyson Fan Heater," located at <http://www.vissbiz.com/dyson-fan-heater-review/cozy-up-to-dyson-fan-heater/> visited on Sep. 3, 2014. (3 pages).

\* cited by examiner

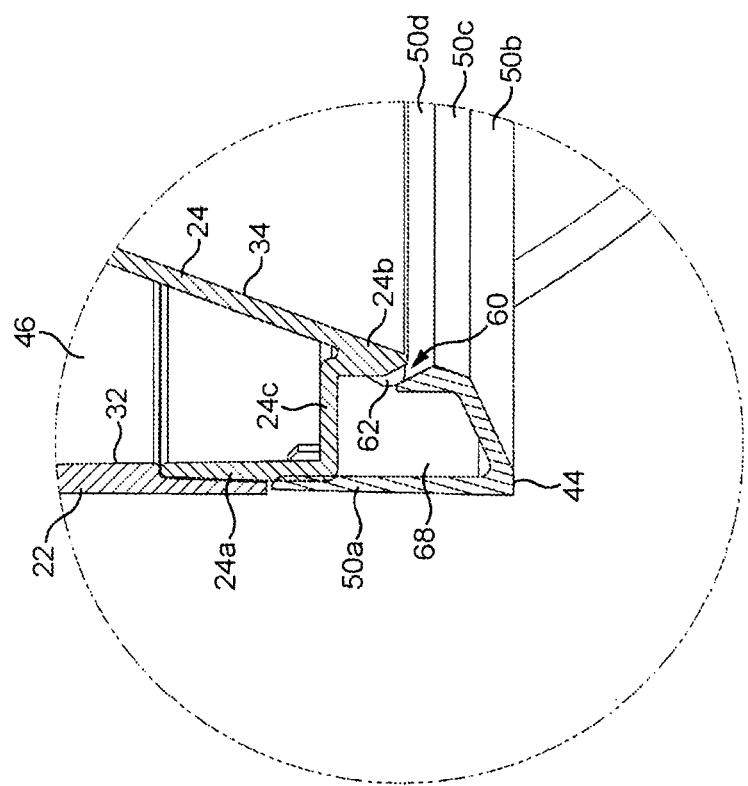
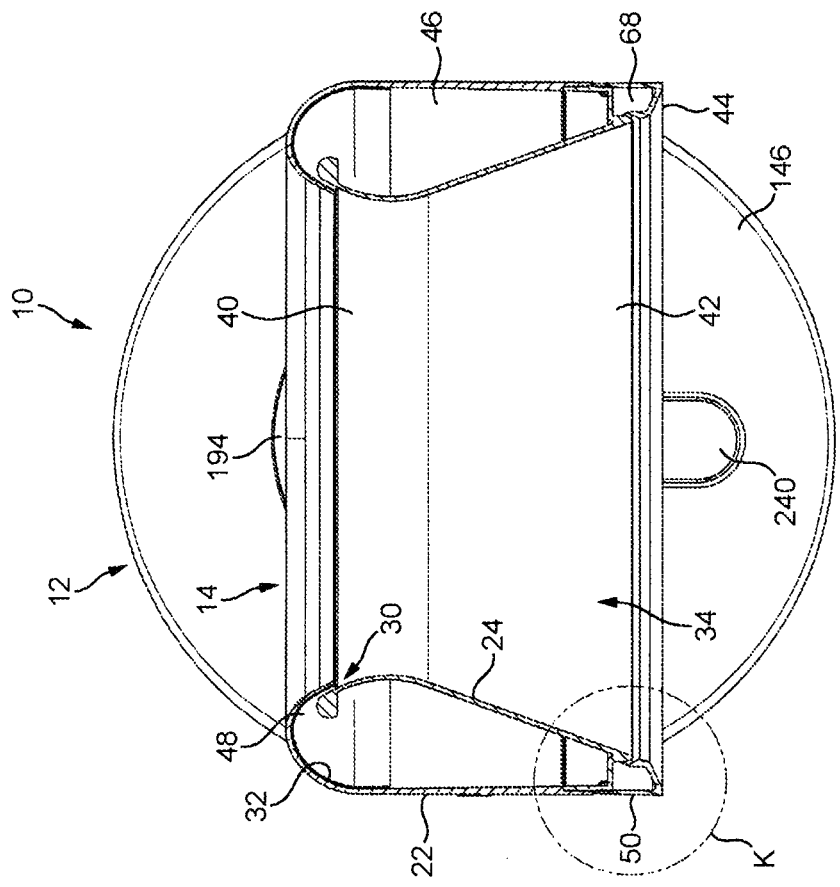
FIG. 6(b)
FIG. 6(a)

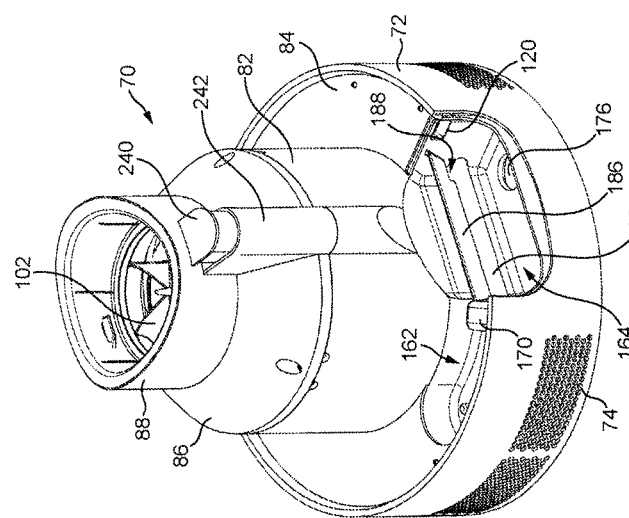
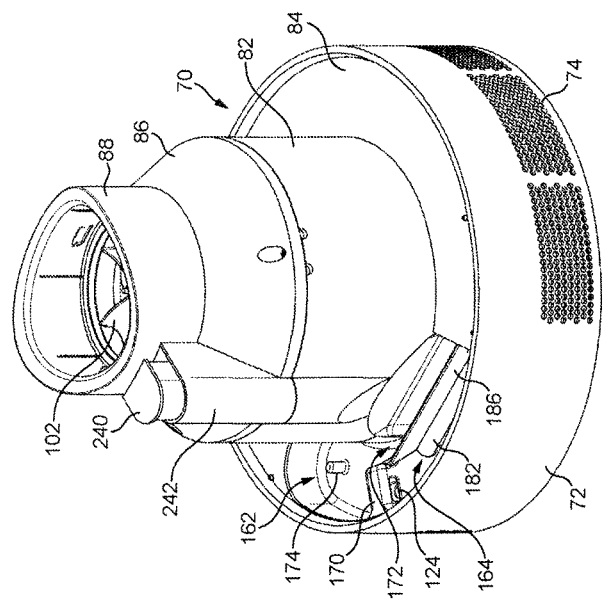

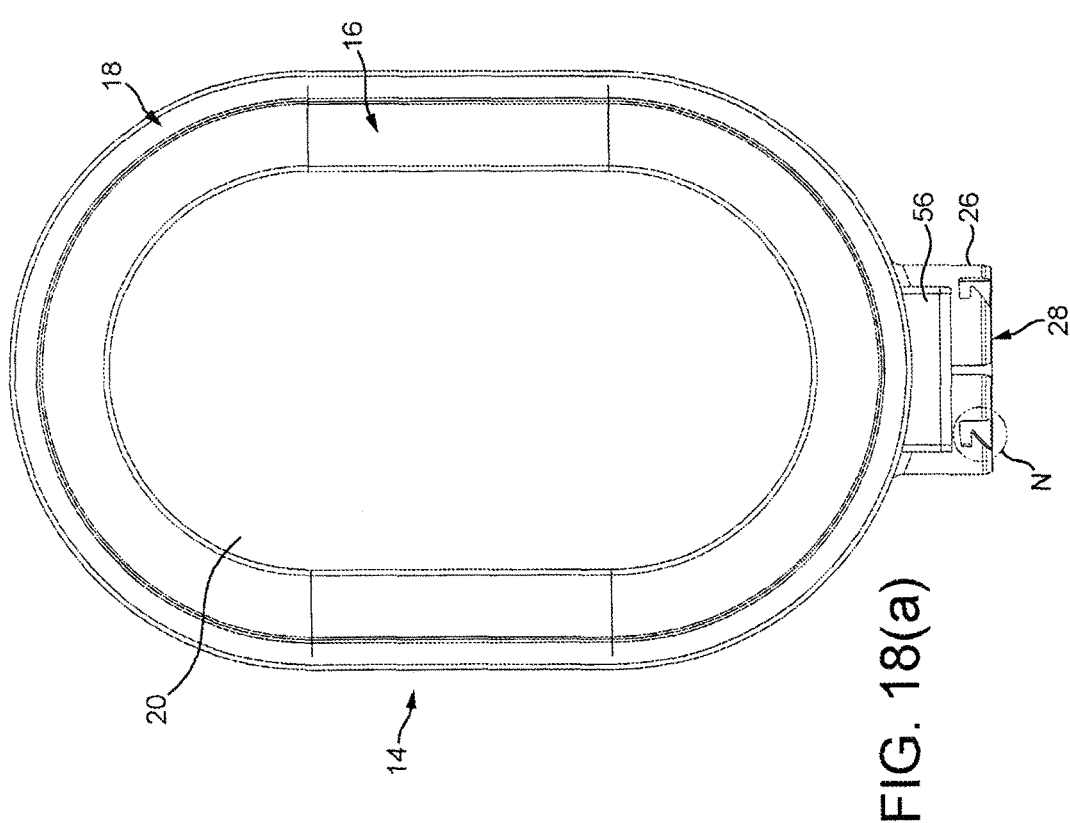

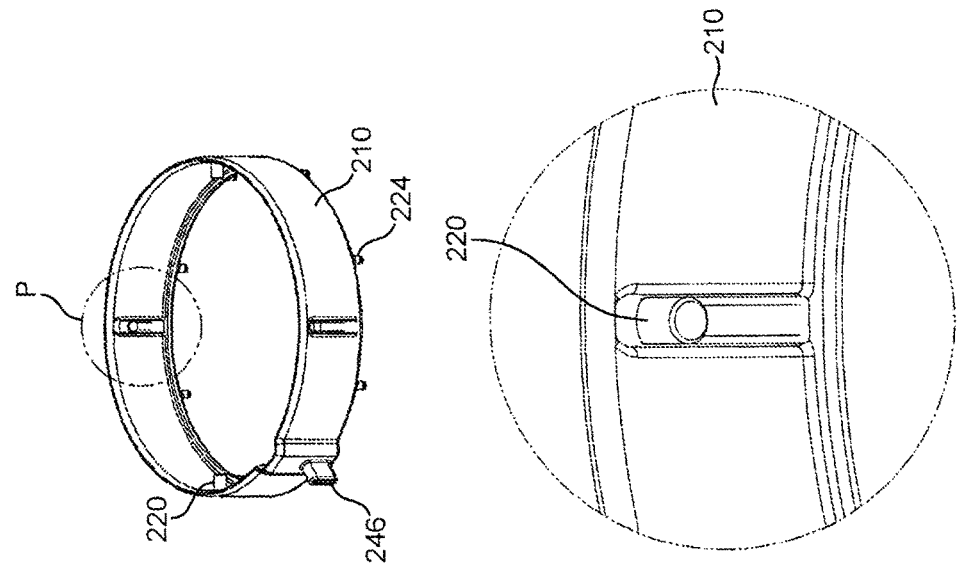
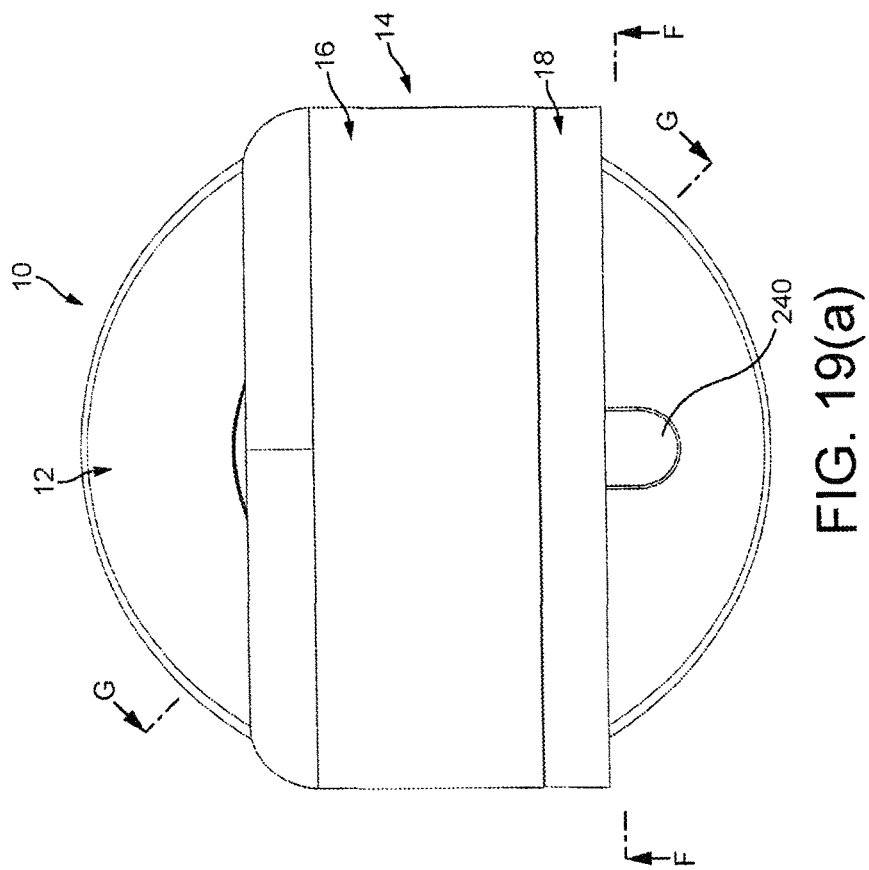

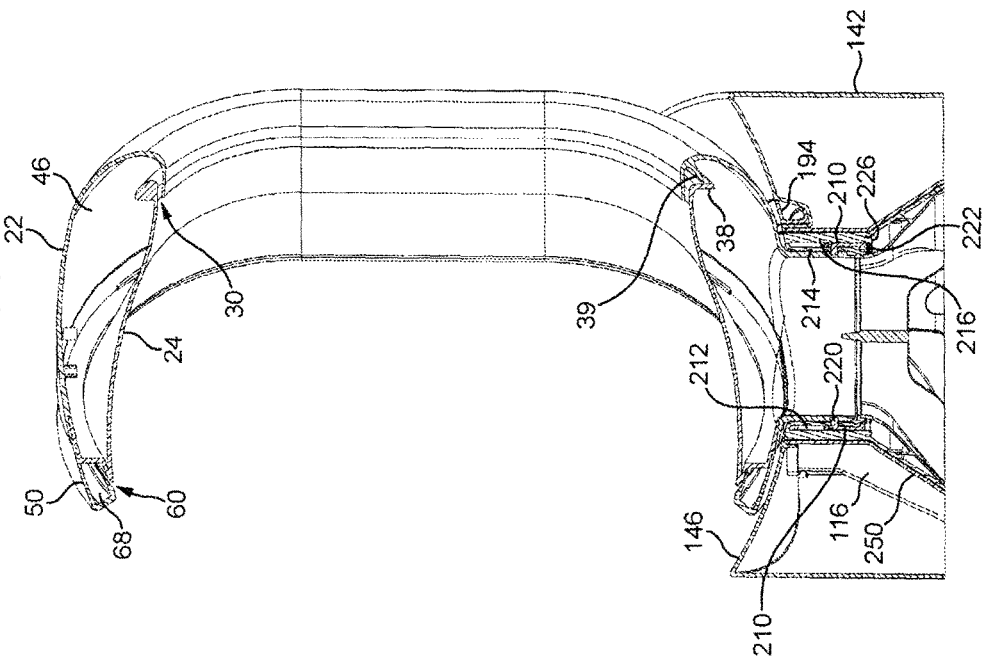

FAN ASSEMBLY

REFERENCE TO RELATED APPLICATIONS

This application claims the priority of United Kingdom Application No. 1301573.0, filed Jan. 29, 2013, the entire contents of which are incorporated herein by reference.

FIELD OF THE INVENTION

The present invention relates to a fan assembly. In a preferred embodiment, the present invention provides a humidifying apparatus for generating a flow of moist air and a flow of air for dispersing the moist air within a domestic environment, such as a room, office or the like.

BACKGROUND OF THE INVENTION

Domestic humidifying apparatus is generally in the form of a portable appliance having a casing comprising a water tank for storing a volume of water, and a fan for creating a flow of air through an air duct of the casing. The stored water is conveyed, usually under gravity, to an atomizing device for producing water droplets from the received water. This device may be in the form of a heater or a high frequency vibrating device, such as a transducer. The water droplets enter the flow of air passing through the air duct, resulting in the emission of a mist into the environment. The appliance may include a sensor for detecting the relative humidity of the air in the environment. The sensor outputs a signal indicative of the detected relative humidity to a drive circuit, which controls the transducer to maintain the relative humidity of the air in the environment around a desired level. Typically, the actuation of the transducer is stopped when the detected relative humidity is around 5% higher than the desired level, and is restarted when the detected relative humidity is around 5% lower than the desired level.

It is known to provide a ultraviolet (UV) lamp or other UV radiation generator to sterilize water that is conveyed to the atomizing device. For example, U.S. Pat. No. 5,859,952 describes a humidifier in which the water supplied from a tank is conveyed through a sterilizing chamber before being conveyed by a pipe to a chamber containing an ultrasonic atomizer. The sterilizing chamber has a UV transparent window beneath which a UV lamp is located to irradiate water as it passes through the sterilizing chamber. U.S. Pat. No. 7,540,474 describes a humidifier in which the water tank includes a UV transparent tube for conveying water to an outlet of the tank, and a main body upon which the tank is mounted includes a UV lamp which irradiates water as it passes through the tube to the outlet.

SUMMARY OF THE INVENTION

In a first aspect, the present invention provides humidifying apparatus comprising:

a chamber;

a water tank for supplying water to the chamber;

at least one baffle located within the chamber for dividing the chamber into an inlet section and an outlet section, and for guiding water received from the water tank along the inlet section to the outlet section;

irradiating means for irradiating water in both the inlet section and the outlet section of the chamber;

atomizing means for atomizing water stored in the outlet section of the chamber;

air flow generating means for generating an air flow over water stored in the outlet section of the chamber; and at least one air outlet for emitting the air flow.

The invention can enable a humidifying apparatus to have a compact appearance through both irradiating and atomizing water stored within a common chamber. To enable the number of bacteria within the stored water to be reduced before the atomization of the stored water takes place, the chamber is divided into an inlet section and an outlet section by at least one baffle located in the chamber. The inlet section and the outlet section each form part of the chamber; the level of water within each section of the chamber is substantially the same. The depth of water within the inlet section and the outlet section may be different; in a preferred embodiment the inlet section is shallower than the outlet section.

The baffle(s) serve to guide water entering the chamber along the inlet section and into the outlet section of the chamber. As it passes along the inlet section, the water is subjected to irradiation by ultraviolet radiation emitted by the irradiating means to reduce the number of bacteria within the water. Within the outlet section of the chamber, the water is further irradiated with ultraviolet radiation emitted by the irradiating means before it is atomized.

Each of the inlet section and the outlet section of the chamber is preferably partially delimited by the irradiating means. The irradiating means preferably comprises one or more lamps or other form of ultraviolet radiation (UV) generator, and one or more transparent sections through which the generated ultraviolet radiation is emitted into the chamber. For example, the inlet section of the chamber may comprise a first transparent section of the irradiating means, and the outlet section may comprise a second transparent section of the irradiating means. Each transparent section may form a window of its respective section of the outlet chamber. These transparent sections of the irradiating means may be arranged to receive ultraviolet radiation from a respective UV generator, or from a common UV generator. These transparent sections of the irradiating means may be spaced from each other. However, in a preferred embodiment the at least one baffle is arranged to divide the irradiating means into a first portion for irradiating water in the inlet section of the chamber, and a second portion for irradiating water in the outlet section of the chamber. The first portion may be contiguous with the second portion. The at least one baffle may comprise a single baffle which extends along the irradiating means. A lower end of the baffle may engage an external surface of the irradiating means to divide it into the first and second portions.

In a preferred embodiment, the irradiating means comprises an ultraviolet radiation transparent section, and the at least one baffle is arranged to engage the transparent section to divide the irradiating means into the first portion and the second portion. The transparent section of the irradiating means is preferably convex in shape, and in a preferred embodiment the transparent section of the irradiating means is tubular in shape, and surrounds a UV lamp or other UV generator. The tube is preferably arranged such that a first portion of the tube provides a lower surface of the inlet section of the chamber, and a second portion of the tube provides at least part of a side wall of the outlet section of the chamber. This lower surface of the inlet section of the chamber may be in the form of a shelf located within the chamber, and which is provided by the upper portion of the tube. As the chamber fills with water, the baffle guides the incoming water along the shelf to enter the outlet section of the chamber.

The baffle may be connected to the tube. Alternatively, the baffle may be connected to, and extend between, opposing side walls of the chamber. The baffle is arranged to engage the outer surface of the tube.

The irradiating means is preferably located within the chamber, and is preferably located adjacent to a side wall of the chamber. In a second aspect the present invention provides humidifying apparatus comprising:

a chamber;

a water tank for supplying water to the chamber;

an ultraviolet radiation generator located within an ultraviolet radiation transparent tube, the tube being located at least partially within the chamber;

at least one baffle located within the chamber for dividing the chamber into an inlet section partially delimited by a first portion of the tube and an outlet section partially delimited by a second portion of the tube, and for guiding water entering the chamber along the inlet section of the chamber to the outlet section of the chamber;

atomizing means for atomizing water in the outlet section of the chamber;

air flow generating means for generating an air flow over water in the outlet section of the chamber; and at least one air outlet for emitting the air flow.

The baffle is preferably arranged to define, at least in part, an aperture through which water flows from the inlet section to the outlet section. The aperture is preferably formed in the lower end of the baffle, and is located at the other end of the chamber from which water enters the chamber from the water tank. The aperture is preferably located adjacent the irradiating means, and is preferably arranged to convey water over the external surface of the irradiating means as it passes from the inlet section to the outlet section.

The humidifying apparatus preferably comprises an inlet duct for conveying the air flow towards the outlet section of the chamber, and an outlet duct for conveying the air flow away from the outlet section of the chamber. The inlet duct preferably comprises an outlet port arranged to emit the air flow in such a direction as to generate a movement of the water stored in the outlet section of the chamber, and thus along or adjacent the portion of the irradiating means for irradiating water in the outlet section of the chamber. The outlet port of the inlet duct is preferably located in a side wall of the chamber, and is preferably arranged to emit air in a direction which is substantially parallel to the upper surface of water stored in the chamber.

The humidifying apparatus preferably comprises a base upon which the water tank is mounted. The base preferably comprises the chamber, the air flow generating means and the inlet duct, with the water tank comprising the outlet duct. The chamber preferably forms part of a water reservoir connected to the base. The water reservoir preferably comprises an inlet chamber for receiving water from the water tank, and for conveying water to said chamber. Part of the outlet duct is preferably removable from the water tank to facilitate cleaning of the internal surfaces of the outlet duct.

The atomizing means preferably comprises a transducer. The humidifying apparatus preferably comprises control means for controlling the irradiating means and the frequency of vibration of the transducer. The control means is preferably arranged to actuate at least one of the irradiating means and the air flow generating means prior to actuation of the transducer. During the period of time in which the irradiation is performed prior to the atomization of stored water, the water stored in the chamber is agitated to generate a flow or swirl of water within the chamber, and which conveys water through the UV radiation emitted into the outlet section of the chamber. This can increase the volume of the stored water which is irradiated with UV radiation prior to the atomization of the stored water, and thus increase the rate of reduction of the number of bacteria within the water stored in the chamber.

The duration of the period of time for which the stored water is irradiated with UV radiation prior to the commencement of the atomization of stored water will depend, inter alia, on the volume of the chamber and the desired reduction in the number of bacteria within the stored water. For example, the duration of this period of time may be in the range from 10 to 300 seconds to achieve an appropriate reduction in the number of bacteria within the maximum volume of water which can be stored in the chamber. The duration may be reduced depending on the length of time which has elapsed since the humidifying apparatus was previously operated. The duration of the period of time for which water is irradiated prior to atomization may be set automatically to a maximum value when the water tank is removed from the base, for example for replenishment.

The humidifying apparatus preferably comprises a nozzle for receiving the air flow, the nozzle comprising said at least one air outlet, the nozzle extending about an opening through which air from outside the apparatus is drawn by air emitted from the nozzle.

Features described above in connection with the first aspect of the invention are equally applicable to the second aspect of the invention, and vice versa.

BRIEF DESCRIPTION OF THE INVENTION

An embodiment of the present invention will now be described, by way of example only, with reference to the accompanying drawings, in which:

FIG. 1 is a front perspective view of a humidifying apparatus;

FIG. 2 is a front view of the humidifying apparatus;

FIG. 3 is a side view of the humidifying apparatus;

FIG. 4 is a rear view of the humidifying apparatus;

FIG. 5(*a*) is a top view of a nozzle of the humidifying apparatus, and FIG. 5(*b*) is a bottom view of the nozzle;

FIG. 6(*a*) is a top sectional view taken along line B-B in FIG. 2, and FIG. 6(*b*) is a close-up of area K indicated in FIG. 6(*a*);

FIG. 7(*a*) is a side sectional view taken along line E-E in FIG. 5(*a*), FIG. 7(*b*) is a close-up of area L indicated in FIG. 7(*a*), and FIG. 7(*c*) is a close-up of area M indicated in FIG. 7(*a*);

FIG. 8 is a front perspective view of the nozzle, with a front casing section of the nozzle detached from the remainder of the nozzle;

FIG. 9(*a*) is a perspective view, from above, of the base of the humidifying apparatus, FIG. 9(*b*) is a similar view to FIG. 9(*a*) following a partial rotation of the base, and with an outer wall of the base partially removed, FIG. 9(*c*) is a similar view to FIG. 9(*a*) following a further partial rotation of the base, with a number of external walls of the base partially removed, and FIG. 9(*d*) is a close-up of area R indicated in FIG. 9(*c*);

FIG. 10 is a top view of the base;

FIG. 11 is a side sectional view taken along line A-A in FIG. 2;

FIG. 12 is a perspective rear view, from above, of a water tank mounted on the base, with the handle in a deployed position;

FIG. 18(*a*) is a front view of the nozzle, and FIG. 18(*b*) is close-up of area N indicated in FIG. 18(*a*);

FIG. 19(*a*) is a top view of the humidifying apparatus, FIG. 19(*b*) is a sectional view taken along line F-F in FIG. 19(*a*), and FIG. 19(*c*) is a sectional view taken along line G-G in FIG. 19(*a*);

FIG. 21(*a*) is a perspective view of a collar of the base, and FIG. 21(*b*) is close-up of area P indicated in FIG. 21(*a*);

DETAILED DESCRIPTION OF THE INVENTION

Figure 1:
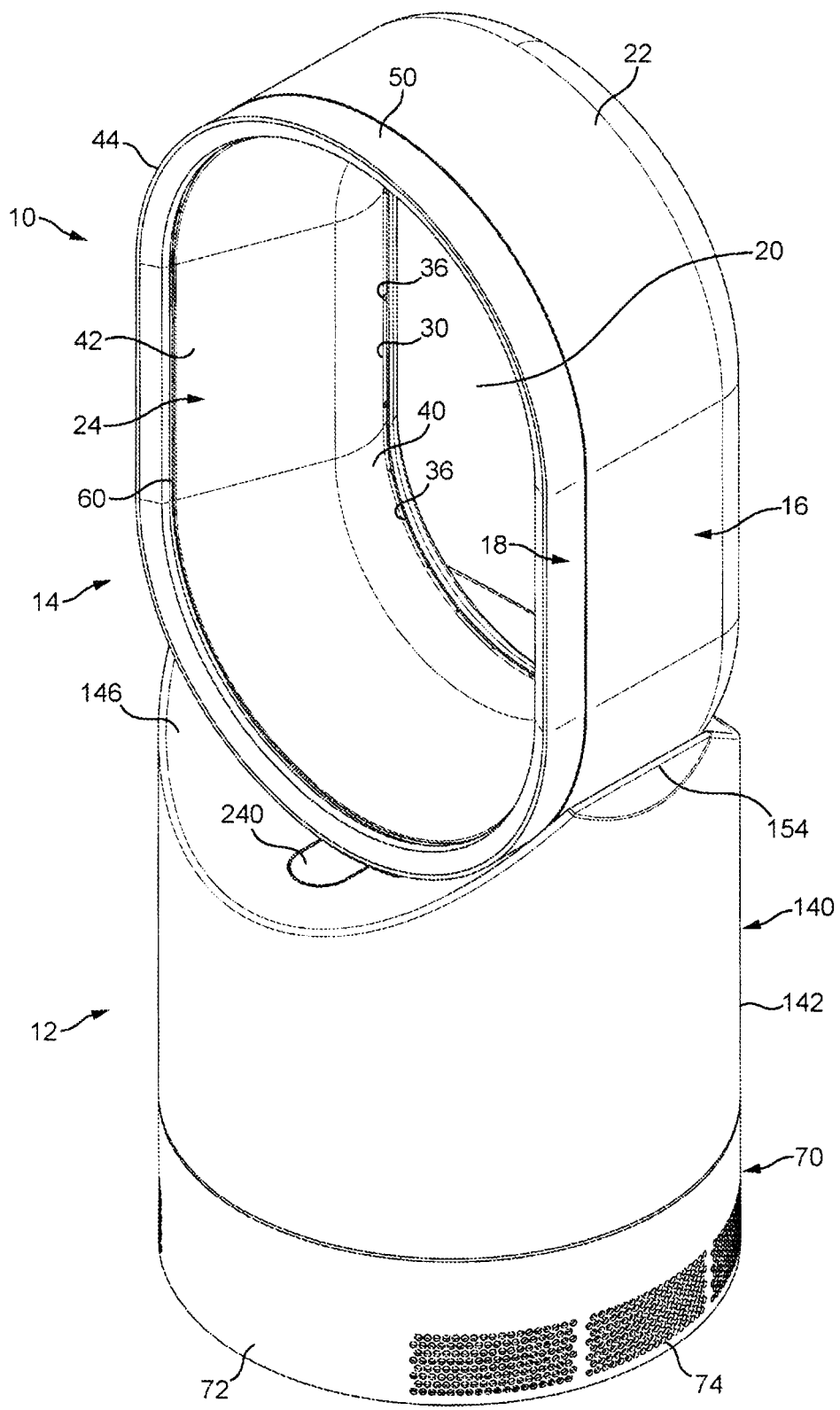
Figure 2:
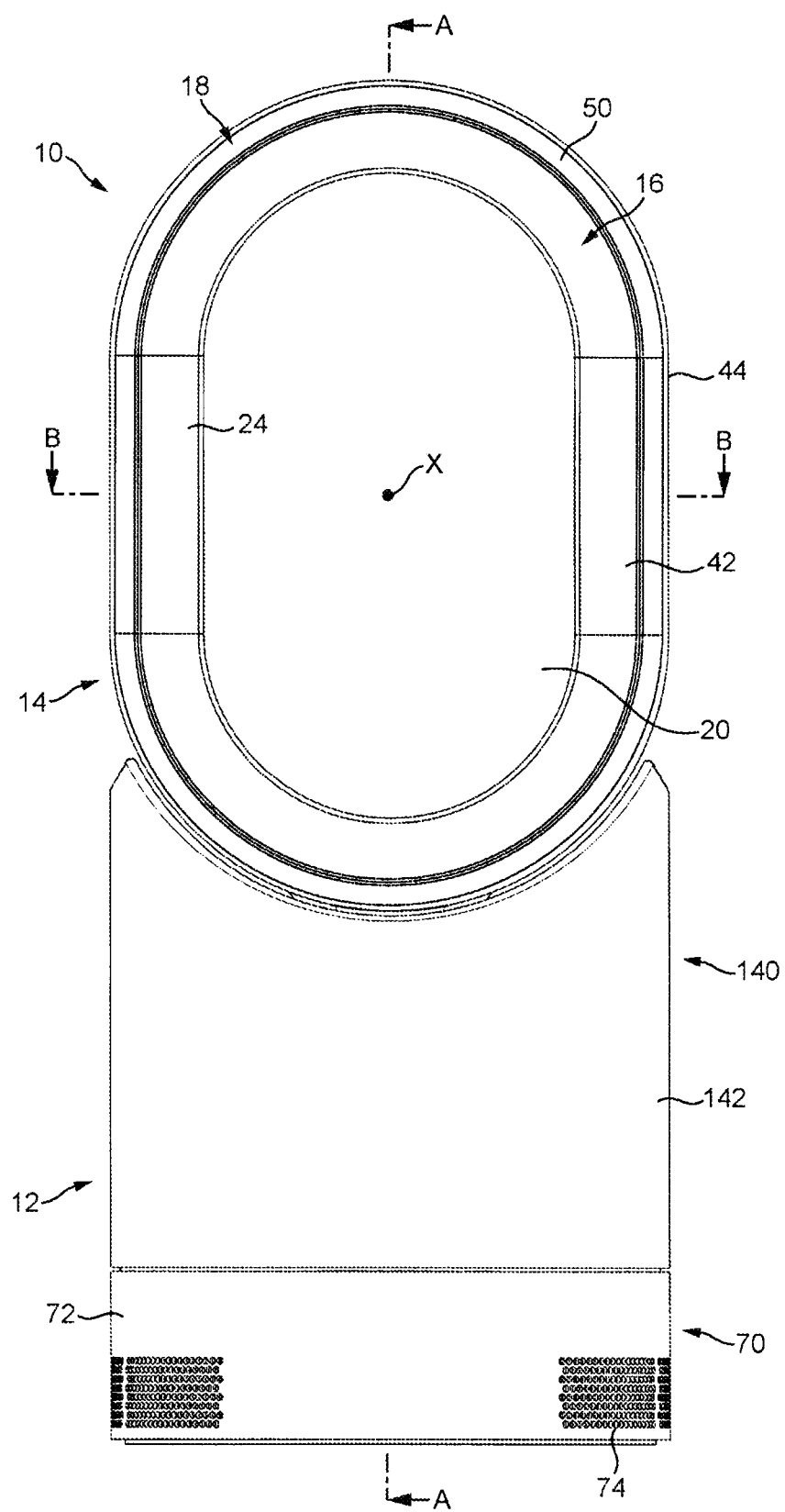
Figure 3:
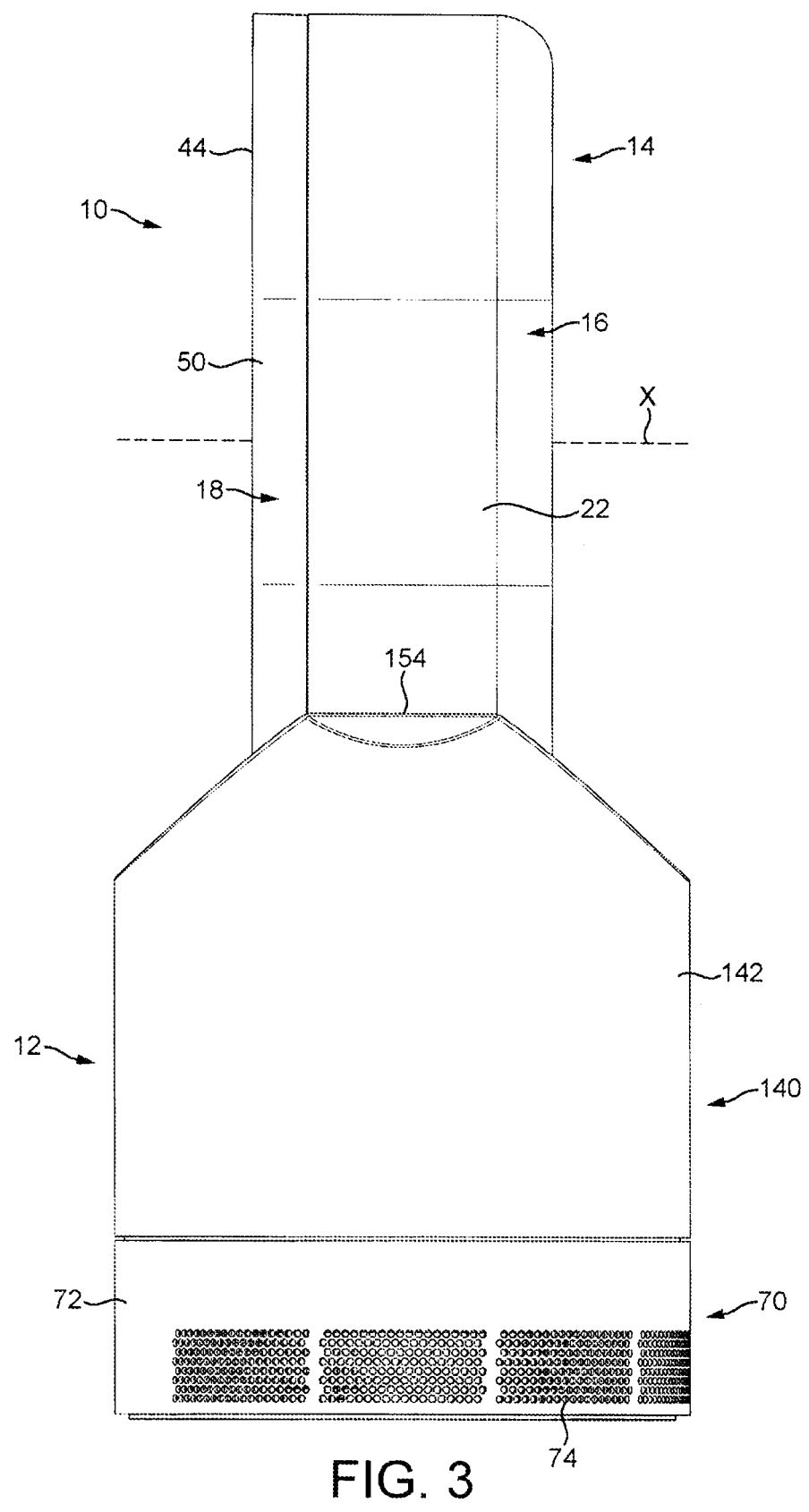
Figure 4:
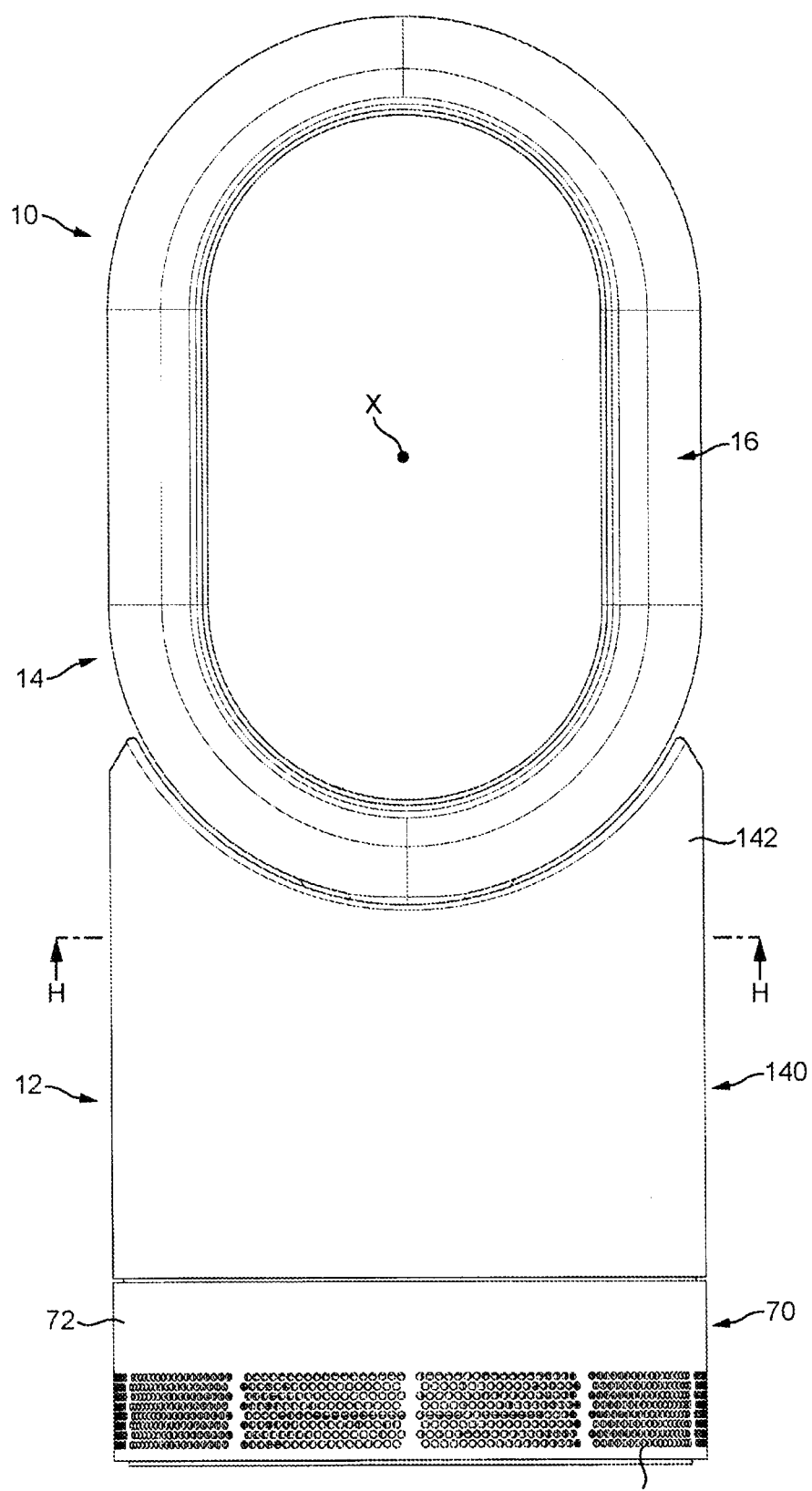
Figure 5A:
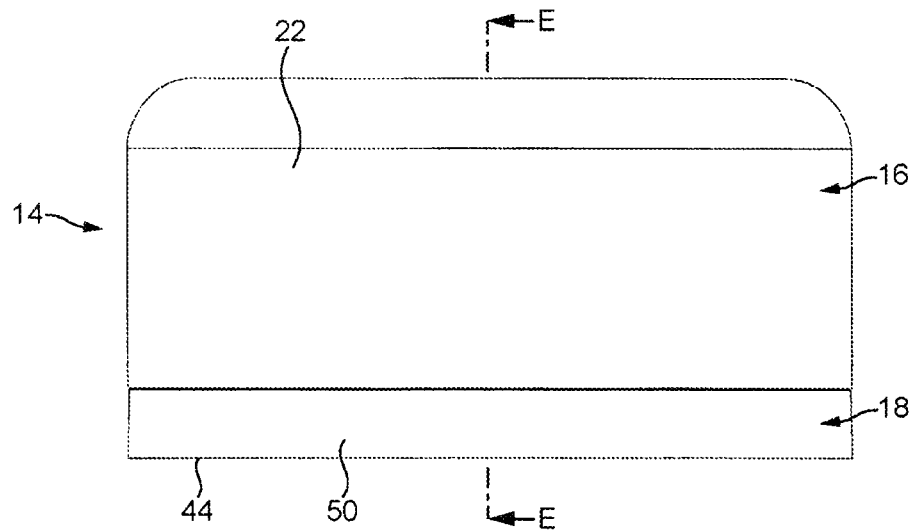
Figure 5B:
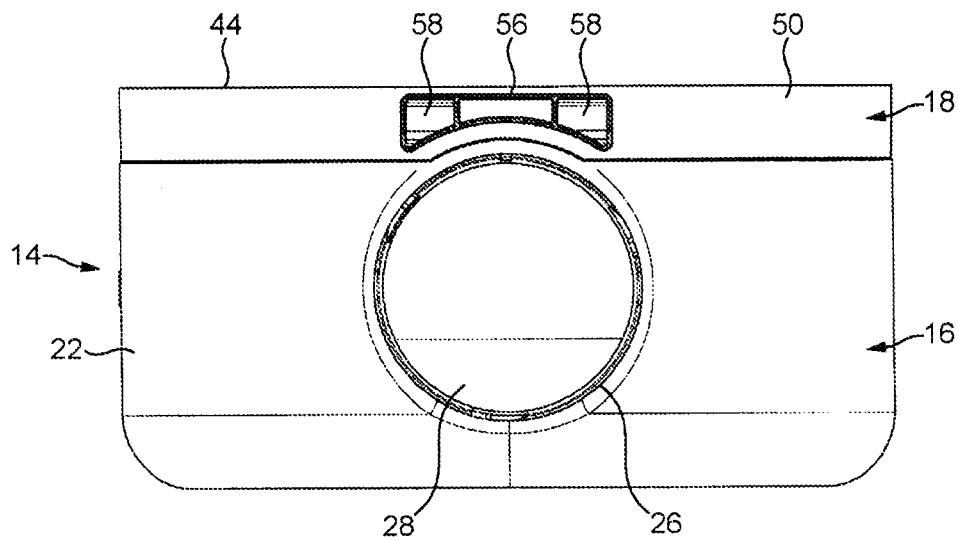

FIGS. 1 to 4 are external views of a fan assembly. In this example, the fan assembly is in the form of a humidifying apparatus 10. In overview, the humidifying apparatus 10 comprises a body 12 comprising an air inlet through which air enters the humidifying apparatus 10, and a nozzle 14 in the form of an annular casing mounted on the body 12, and which comprises a plurality of air outlets for emitting air from the humidifying apparatus 10.

The nozzle 14 is arranged to emit two different air flows. The nozzle 14 comprises a rear section 16 and a front section 18 connected to the rear section 16. Each section 16, 18 is annular in shape, and extends about a bore 20 of the nozzle 14. The bore 20 extends centrally through the nozzle 14 so that the centre of each section 16, 18 is located on the axis X of the bore 20.

In this example, each section 16, 18 has a "racetrack" shape, in that each section 16, 18 comprises two, generally straight sections located on opposite sides of the bore 20, a curved upper section joining the upper ends of the straight sections and a curved lower section joining the lower ends of the straight sections. However, the sections 16, 18 may have any desired shape; for example the sections 16, 18 may be circular or oval. In this embodiment, the height of the nozzle 14 is greater than the width of the nozzle, but the nozzle 14 may be configured so that the width of the nozzle 14 is greater than the height of the nozzle 14.

Each section 16, 18 of the nozzle 14 defines a flow path along which a respective one of the air flows passes. In this embodiment, the rear section 16 of the nozzle 14 defines a first air flow path along which a first air flow passes through the nozzle 14, and the front section 18 of the nozzle 14 defines a second air flow path along which a second air flow passes through the nozzle 14.

With reference also to FIGS. 5 to 8, the rear section 16 of the nozzle 14 comprises an annular outer casing section 22 connected to and extending about an annular inner casing section 24. Each casing section 22, 24 extends about the bore axis X. Each casing section may be formed from a plurality of connected parts, but in this embodiment each casing section 22, 24 is formed from a respective, single moulded part. Each casing section 22, 24 is preferably formed from plastics material. As shown in FIG. 6(*b*), the front part of the inner casing section 24 has an annular outer wall 24*a* which extends generally parallel to the bore axis X, a front end wall 24*b* and an annular intermediary wall 24*c* which extends generally perpendicular to the bore axis X and which joins the outer wall 24*a* to the end wall 24*b* so that the end wall 24*b* protrudes forwardly beyond the intermediary wall 24*c*. During assembly, the external surface of the outer wall 24*a* is connected to the internal surface of the front end of the outer casing section 22, for example using an adhesive.

The outer casing section 22 comprises a tubular base 26 which defines a first air inlet 28 of the nozzle 14. The outer casing section 22 and the inner casing section 24 together define a first air outlet 30 of the nozzle 14. The first air outlet 30 is defined by overlapping, or facing, portions of the internal surface 32 of the outer casing section 22 and the external surface 34 of the inner casing section 24. The first air outlet 30 is in the form of a slot. The slot has a relatively constant width in the range from 0.5 to 5 mm. In this example the first air outlet has a width of around 1 mm. Spacers 36 may be spaced about the first air outlet 30 for urging apart the overlapping portions of the outer casing section 22 and the inner casing section 24 to control the width of the first air outlet 30. These spacers may be integral with either of the casing sections 22, 24.

In this embodiment, the first air outlet 30 extends partially about the bore 20. The first air outlet 30 extends along the curved upper section and the straight sections of the nozzle 14. However, the first air outlet 30 may extend fully about the bore 20. The nozzle 14 includes a first sealing member 38 for inhibiting the emission of the first air flow from the curved lower section of the nozzle 14. In this embodiment, the first sealing member 38 is located on and preferably integral with the inner casing section 24. The first sealing member 38 is generally U-shaped. The first sealing member 38 is located on the rear end of the inner casing section 24, and lies in a plane which is substantially perpendicular to the axis X. The end of the first sealing member 38 engages a U-shaped protrusion 39 extending forwardly from the rear end of the curved lower section of the outer casing section 22 to form a seal therewith.

The first air outlet 30 is arranged to emit air through a front part of the bore 20 of the nozzle 14. The first air outlet 30 is shaped to direct air over an external surface of the nozzle 14. In this embodiment, the external surface 34 of the inner casing section 24 comprises a Coanda surface 40 over which the first air outlet 30 is arranged to direct the first air flow. The Coanda surface 40 is annular, and thus is continuous about the central axis X. The external surface 34 of the inner casing section 24 also includes a diffuser portion 42 which tapers away from the axis X in a direction extending from the first air outlet 30 to the front end 44 of the nozzle 14.

The casing sections 22, 24 together define an annular first interior passage 46 for conveying the first air flow from the first air inlet 28 to the first air outlet 30. The first interior passage 46 is defined by the internal surface of the outer casing section 22 and the internal surface of the inner casing section 24. A tapering, annular mouth 48 of the rear section 16 of the nozzle 14 guides the first air flow to the first air outlet 30. The first air flow path through the nozzle 14 may therefore be considered to be formed from the first air inlet 28, the first interior passage 46, the mouth 48 and the first air outlet 30.

The front section 18 of the nozzle 14 comprises an annular front casing section 50. The front casing section 50 extends about the bore axis X, and has a "racetrack" shape which is similar to that of the other casing sections 22, 24 of the nozzle 14. Similar to the casing sections 22, 24, the front casing section 50 may be formed from a plurality of connected parts, but in this embodiment the front casing section 50 is formed from a single moulded part. The front casing section 50 is preferably formed from plastics material. As explained in more detail below, the front casing section 50 is detachably attached to the remainder of the nozzle 14. In this embodiment, the front casing section 50 is detachably attached to the inner casing section 24, but depending on the arrangement of the outer casing section 22 and the inner casing section 24 the front casing section 50 may be detachably attached to the outer casing section 22. In this embodiment, a snap-fit connection is used to connect the front casing section 50 to the remainder of the nozzle 14 but other methods for connecting the front casing section 50 may be used. For example, one or more magnets may be used to detachably connect the front casing section 50 to the remainder of the nozzle 14.

The front casing section 50 comprises an annular outer wall 50a which extends generally parallel to the bore axis X, an annular inner wall and an annular front wall 50b which connects the outer side wall 50a to the inner wall. The inner wall comprises a front section 50c which extends generally parallel to the front wall 24b of the inner casing section 24, and a rear section 50d which is angled to the front section 50c so that the rear section 50d tapers towards the axis X in a direction extending from the first air outlet 30 to the front end 44 of the nozzle 14.

The front casing section 50 comprises a plurality of catches 52 extending inwardly from the internal surface of the outer wall 50a. Each catch 52 is generally cuboid in shape. The catches 52 are preferably regularly spaced about the bore axis X. The outer wall 24a of the inner casing section 24 comprises a plurality of recesses 54 similarly spaced about the bore axis X for receiving the catches 52. During assembly, the front casing section 50 is pushed on to the front of the inner casing section 24. The outer wall 50a deflects elastically outwardly as each catch 52 slides over the outer wall 24a to enter a respective recess 54. The outer wall 50a relaxes as the catches 52 enter the recesses 54, which prevents the catches 52 from becoming readily removed from the recesses 54, thereby attaching the front casing section 50 to the inner casing section 24.

The lower end of the front casing section 50 comprises a tubular base 56. To subsequently detach the front casing section 50 from the inner casing section 24, the user grasps the base 56 of the front casing section 50 and pulls the front casing section 50 away from the inner casing section 24. The outer wall 50a deforms elastically under the force exerted on the outer wall 50 due to the abutment of the catches 52 with the walls of the recesses 54. If a sufficient pulling force is applied to the front casing section 50 by the user, the outer wall 50a deforms sufficiently to move the catches 52 out from the recesses 54, thereby allowing the front casing section 50 to move away from the inner casing section 24.

The base 56 defines a plurality of second air inlets 58 of the nozzle 14. In this embodiment, the base 56 comprises two second air inlets 58. Alternatively the base 56 may comprises a single air inlet 58. The front casing section 50 defines with the inner casing section 24 a second air outlet 60 of the nozzle 14. In this example, the second air outlet 60 extends partially about the bore 20, along the curved upper section and the straight sections of the nozzle 14. Alternatively, the second air outlet 60 may extend fully about the bore 20. The second air outlet 60 is in the form of a slot having a relatively constant width in the range from 0.5 to 5 mm. In this example the second air outlet 60 has a width of around 1 mm. The second air outlet 60 is located between the internal surface of the end wall 24b of the inner casing section 24 and the external surface of the rear section 50d of the inner wall of the front casing section 50. Spacers 62 may be spaced along the second air outlet 60 to urge apart the overlapping portions of the inner casing section 24 and the front casing section 50 to control the width of the second air outlet 60. These spacers may be integral with either of the casing sections 24, 50.

The second air outlet 60 is configured to emit the second air flow over the external surface of the rear section 50d of the inner wall of the front casing section 50. This surface thus provides a Coanda surface over which each second air outlet 60 is arranged to direct a respective portion of the second air flow. This Coanda surface is also continuous about the axis X, but as the air outlet 60 only extends about part of the bore 20 this Coanda surface may similarly extend about part of the bore 20. The external surface of the front section 50c of the front casing section 50 provides a diffuser portion which tapers away from the axis X in a direction extending from the second air outlet 60 to the front end 44 of the nozzle 14.

Figure 7A:
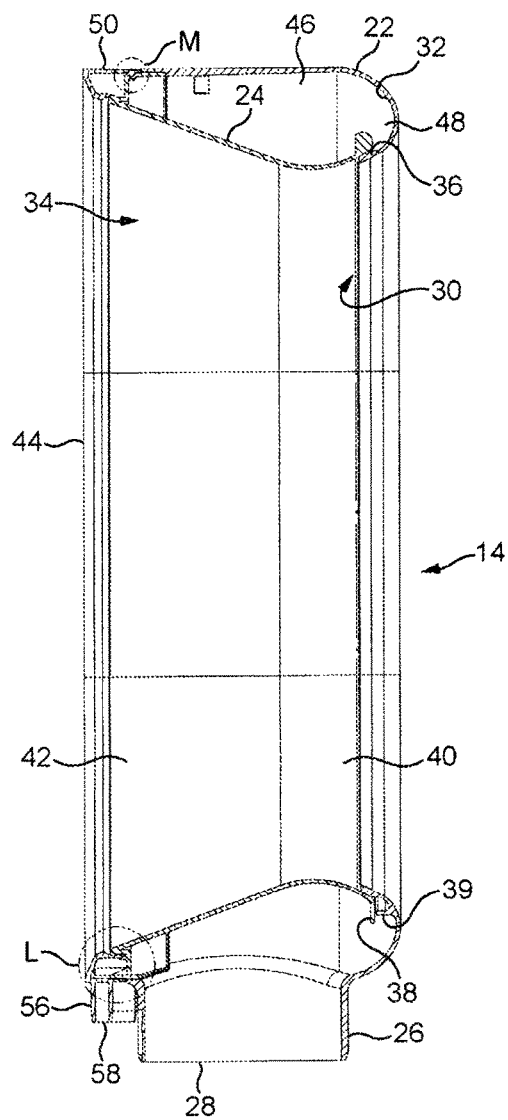
Figure 7B:
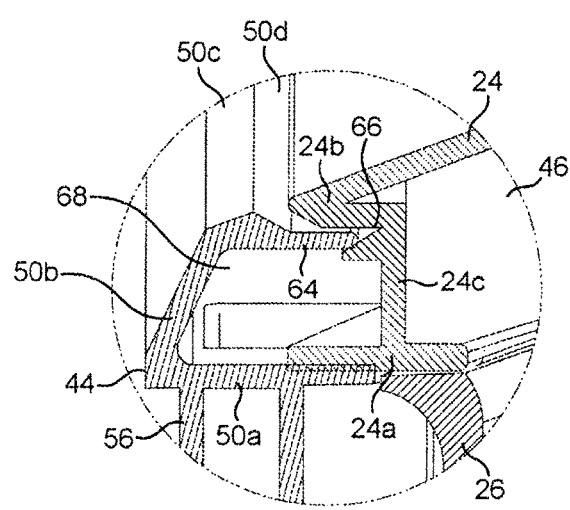
Figure 7C:
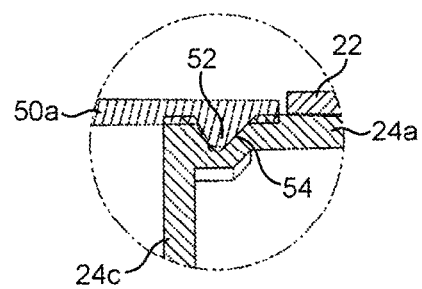
Figure 8:
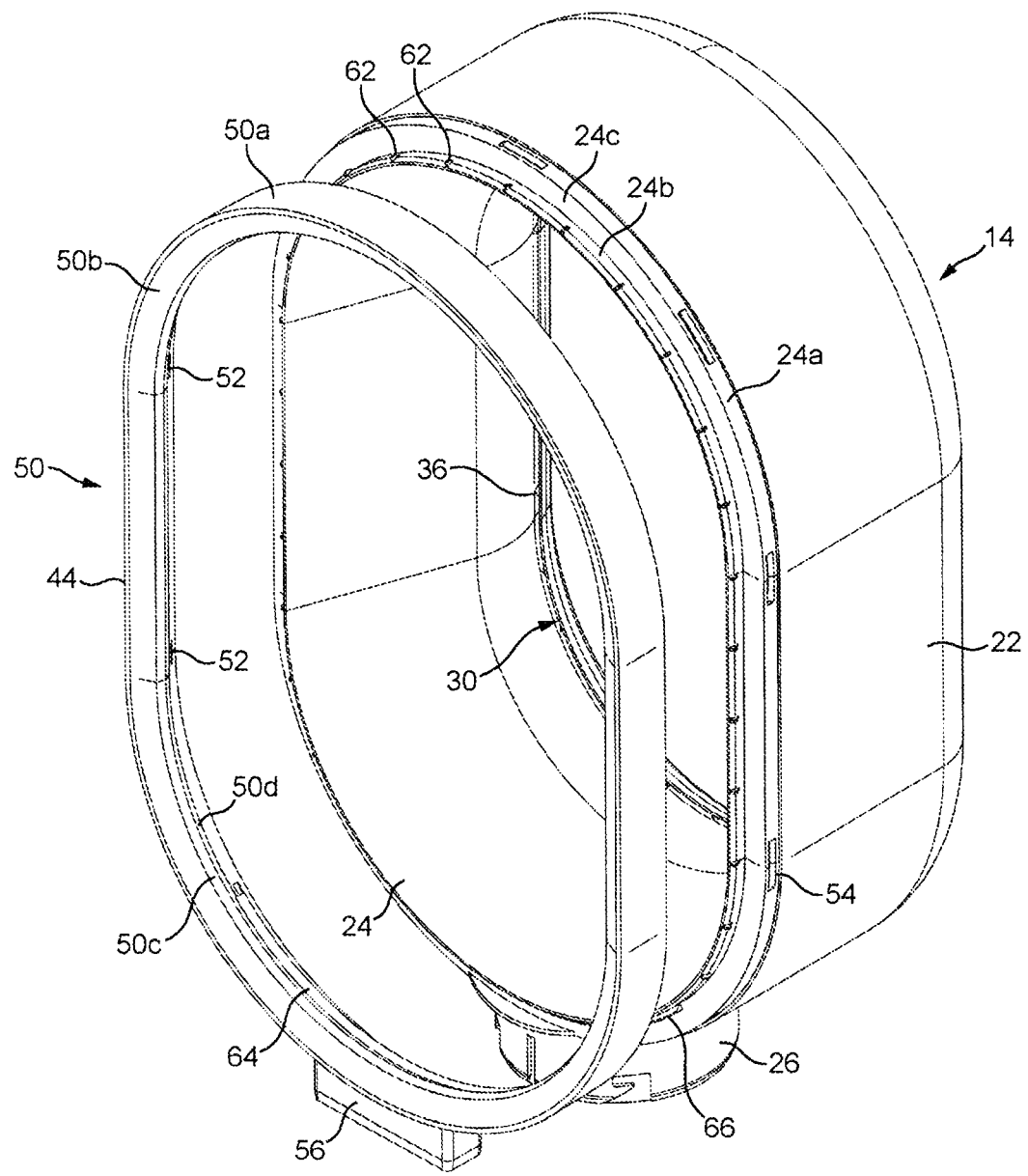

With reference to FIGS. 7(b) and 8, the nozzle 14 comprises a second sealing member 64 for inhibiting the emission of air from the curved lower section of the nozzle 14. In this embodiment, the second sealing member 64 is located on and preferably integral with the front casing section 50. The second sealing member 64 is generally U-shaped. The second sealing member 64 is located on the curved lower section of the front casing section 50, and extends rearwardly from the rear section 50d of the inner wall. When the front casing section 50 is attached to the inner casing section 24, the end of the second sealing member 64 locates within a U-shaped groove located between the end wall 24b and the intermediary wall 24c of the inner casing section 24 to form a seal with the inner casing section 24.

The casing sections 24, 50 together define an annular second interior passage 68 for conveying the second air flow from the second air inlets 58 to the second air outlet 60. The second interior passage 68 is defined by the internal surfaces of the inner casing section 24 and the front casing section 50. The second air flow path through the nozzle 14 may therefore be considered to be formed by the second air inlets 58, the interior passage 68 and the second air outlet 60.

Figure 9C:
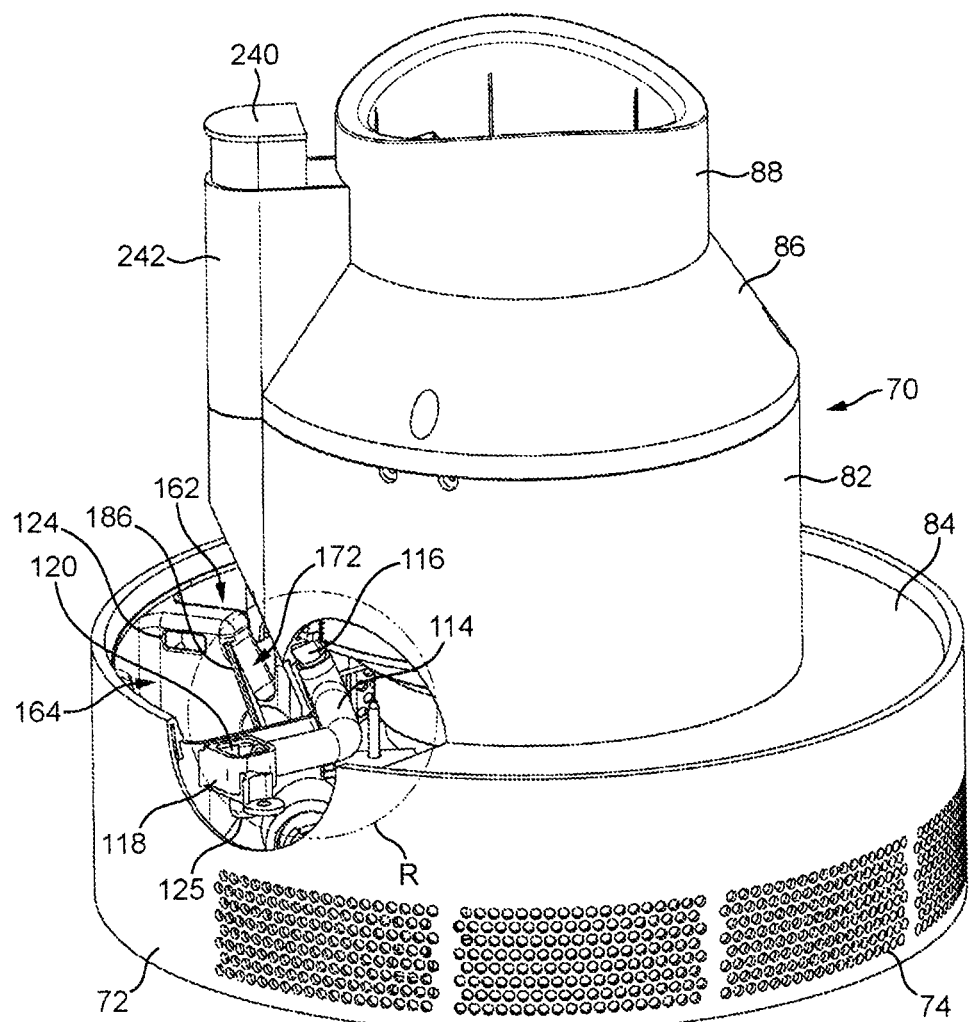
Figure 9D:
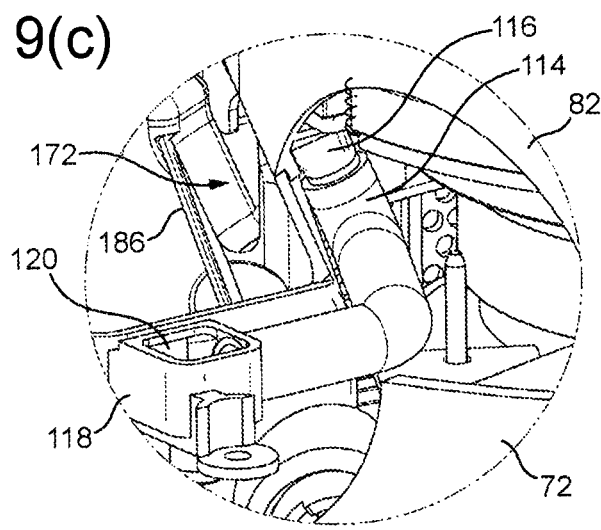
Figure 10:
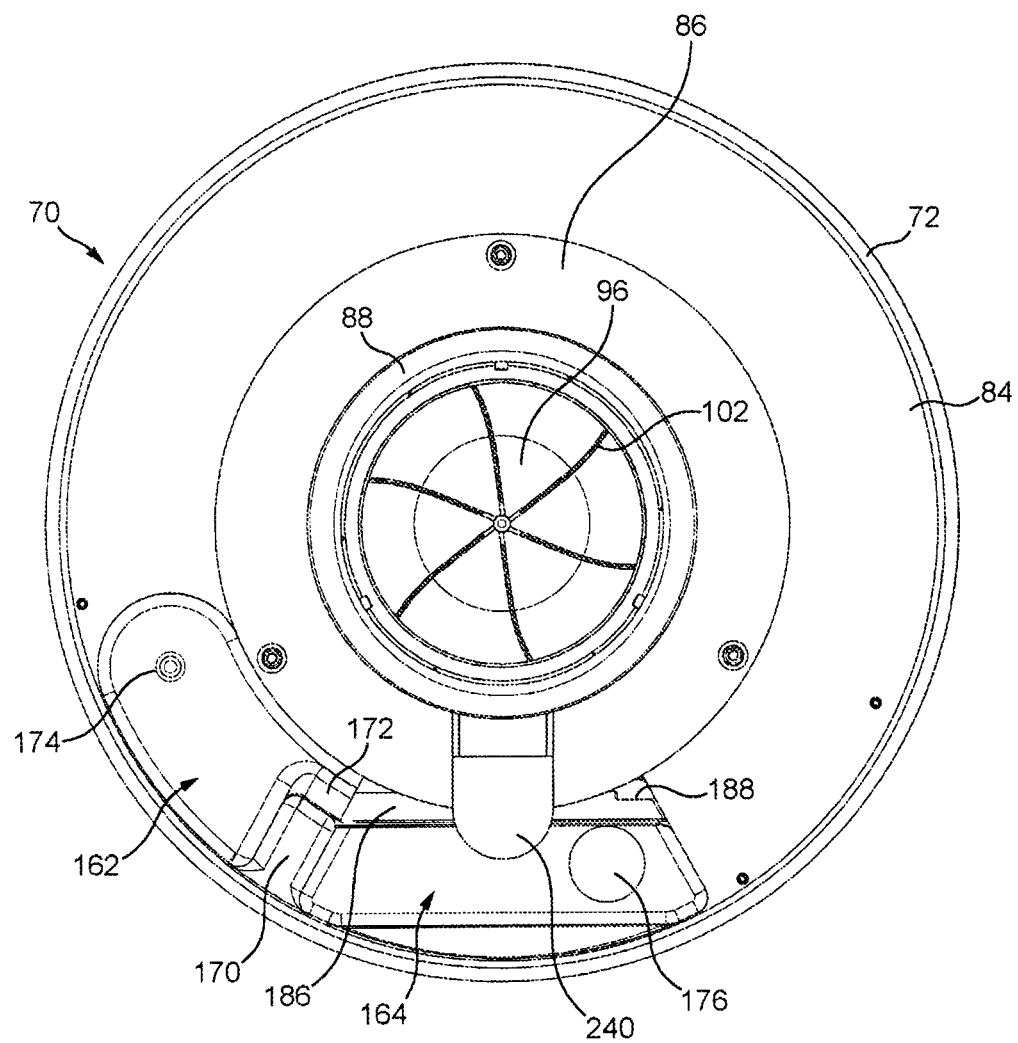

Returning to FIGS. 1 to 4, the body 12 is generally cylindrical in shape. The body 12 comprises a base 70. FIGS. 9 and 10 are external views of the base 70. The base 70 has an external outer wall 72 which is cylindrical in shape, and which comprises an air inlet 74. In this example, the air inlet 74 comprises a plurality of apertures formed in the outer wall 72 of the base 70. A front portion of the base 70 may comprise a user interface of the humidifying apparatus 10. The user interface is illustrated schematically in FIG. 22, and described in more detail below. A mains power cable (not shown) for supplying electrical power to the humidifying apparatus 10 extends through an aperture formed in the base 70.

Figure 11:
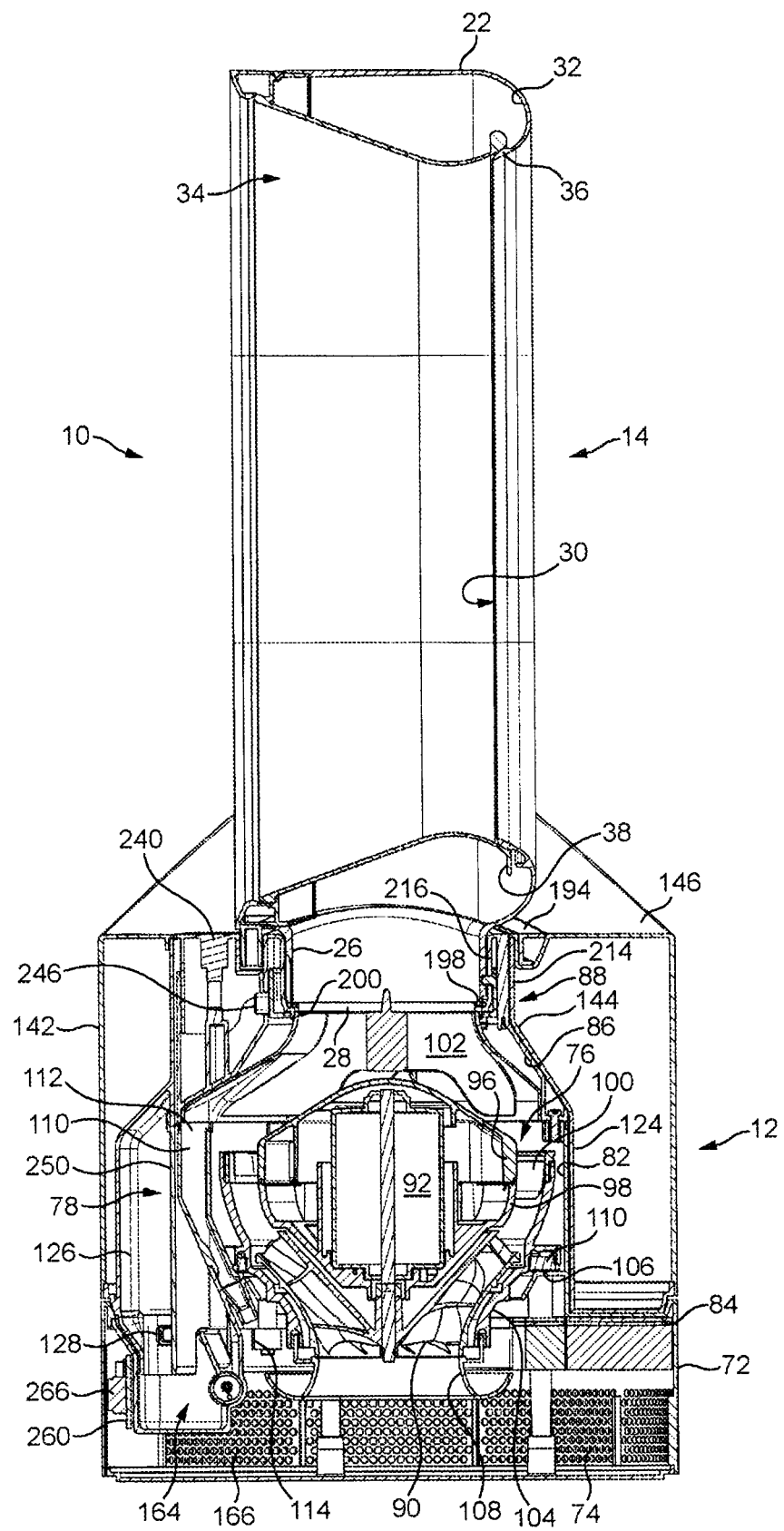

With reference also to FIG. 11, the base 70 comprises a first air passageway 76 for conveying a first air flow to the first air flow path through the nozzle 14, and a second air passageway 78 for conveying a second air flow to the second air flow path through the nozzle 14. The first air passageway 76 passes through the base 70 from the air inlet 74 to the first air inlet 28 of the nozzle 14. The base 70 comprises a flat bottom wall 80 connected to the lower end of the outer wall 72. A tubular central wall 82, having a smaller diameter than the outer wall 72, is connected to the outer wall 72 by an arcuate supporting wall 84. The central wall 82 is substantially co-axial with the outer wall 72. The supporting wall 84 is located above, and generally parallel to, the bottom wall 80. The supporting wall 84 extends partially about the central wall 82 to define an opening for receiving a water reservoir 160 of the base 70, as described in more detail below. The central wall 82 extends upwardly away from the supporting wall 84. In this example, the outer wall 72, central wall 82 and supporting wall 84 are formed as a single component of the base 70, but alternatively two or more of these walls may be formed as a respective component of the base 70. An upper wall of the base 70 is connected to the upper end of the central wall 82. The upper wall has a lower frusto-conical section 86 and an upper cylindrical section 88 into which the base 26 of the nozzle 14 is inserted.

The central wall 82 extends about an impeller 90 for generating a first air flow through the first air passageway 76. In this example the impeller 90 is in the form of a mixed flow impeller. The impeller 90 is connected to a rotary shaft extending outwardly from a motor 92 for driving the impeller 90. In this embodiment, the motor 92 is a DC brushless motor having a speed which is variable by a drive circuit 94 in response to a speed selection by a user. The maximum speed of the motor 92 is preferably in the range from 5,000 to 10,000 rpm. The motor 92 is housed within a motor bucket comprising an upper portion 96 connected to a lower portion 98. The upper portion 96 of the motor bucket comprises a diffuser 100 in the form of a stationary disc having curved blades. The upper wall extends about a plurality of stationary guide vanes 102 for guiding air emitted from the diffuser 100 towards the first air inlet 28 of the nozzle 14. The guide vanes 102 preferably form part of a single molded component connected to the upper wall of the base 70.

The motor bucket is located within, and mounted on, a generally frusto-conical impeller housing 104. The impeller housing 104 is, in turn, mounted on an annular platform 106 extending inwardly from the central wall 82. An annular inlet member 108 is connected to the bottom of the impeller housing 104 for guiding the air flow into the impeller housing 104. An annular sealing member 110 is located between the impeller housing 104 and the platform 106 to prevent air from passing around the outer surface of the impeller housing 104 to the inlet member 108. The platform 106 preferably comprises a guide portion for guiding an electrical cable from the drive circuit 94 to the motor 92.

The first air passageway 76 extends from the air inlet 74 to the inlet member 108. From the inlet member 108, the first air passageway 76 extends, in turn, through the impeller housing 104, the upper end of the central wall 82 and the sections 86, 88 of the upper wall.

The second air passageway 78 is arranged to receive air from the first air passageway 76. The second air passageway 78 is located adjacent to the first air passageway 76. The second air passageway 78 comprises an inlet duct for receiving air from the first air passageway 76. With reference to FIG. 11, the inlet duct comprises a first section 110 which is defined by the central wall 82 of the base 70. The first section of the inlet duct 110 is located adjacent to, and in this example radially external of, part of the first air passageway 76. The first section 110 of the inlet duct has an inlet port 112 located downstream from, and radially outward from, the diffuser 100 so as to receive part of the air flow emitted from the diffuser 100, and which forms the second air flow. With particular reference to FIGS. 9(c) and 9(d), a second section of the inlet duct is defined by a flexible tube 114. The tube 114 extends between a tubular connector 116 for receiving air from the first section 110 of the inlet duct to a manifold 118. The manifold 118 has an outlet port 120. Optionally, the manifold 118 may be connected by a second flexible tube (not shown) to a second manifold 122 having an outlet port 124. Each manifold 118, 122 includes a tubular connector 125 on to which one of the second flexible tube is located to place the manifolds 118, 122 in fluid communication.

The second air passageway 78 further comprises an outlet duct 126 which is arranged to convey the second air flow to the second air inlets 58 of the nozzle 14. The outlet duct 126 comprises two inlet ports 128 located in the side wall of the outlet duct 126, towards the lower end thereof. The inlet ports 128 have substantially the same shape as the outlet ports 120, 124. The outlet duct 126 also comprises two outlet ports 130 located at the upper end thereof. Each of the second air inlets 58 of the nozzle 14 is arranged to receive air from a respective one of the outlet ports 130.

The humidifying apparatus 10 is configured to increase the humidity of the second air flow before it enters the nozzle 14. With reference now to FIGS. 1 to 4 and FIGS. 11 to 14, the humidifying apparatus 10 comprises a water tank 140 removably mountable on the base 70 of the body 12. The water tank 140 has a cylindrical outer wall 142 which has the same radius as the outer wall 72 of the base 70 of the body 12 so that the body 12 has a cylindrical appearance when the water tank 140 is mounted on the base 70. The water tank 140 has a tubular inner wall 144 which surrounds the walls 82, 86, 88 of the base 70 when the water tank 140 is mounted on the base 70. The outer wall 142 and the inner wall 144 define, with an annular upper wall 146 and an annular lower wall 148 of the water tank 140, an annular volume for storing water. The water tank 140 thus surrounds the impeller 90 and the motor 92, and so at least part of the first air passageway 76, when the water tank 140 is mounted on the base 70. The lower wall 148 of the water tank 140 engages, and is supported by, the supporting wall 84 of the base 70 when the water tank 140 is mounted on the base 70.

The outlet duct 126 passes through the water tank 140. A lower portion of the outlet duct 126 protrudes from the lower wall 148 of the water tank 140, and the inlet ports 128 are located in the side wall of this lower portion of the outlet duct 126. The outlet ports 130 are located in a recessed portion 149 of the upper wall 146 of the water tank 140.

The water tank 140 preferably has a capacity in the range from 2 to 4 liters. With reference to FIG. 9, a spout 150 is removably connected to the lower wall 148 of the water tank 140, for example through co-operating threaded connections. In this example the water tank 140 is filled by removing the water tank 140 from the base 70 and inverting the water tank 140 so that the spout 150 is projecting upwardly. The spout 150 is then unscrewed from the water tank 140 and water is introduced into the water tank 140 through an aperture exposed when the spout 150 is disconnected from the water tank 140. Once the water tank 140 has been filled, the user reconnects the spout 150 to the water tank 140, returns the water tank 140 to its non-inverted orientation and replaces the water tank 140 on the base 70. A spring-loaded valve 152 is located within the spout 150 for preventing leakage of water through a water outlet of the spout 150 when the water tank 140 is re-inverted. The valve 152 is biased towards a position in which a skirt of the valve 152 engages the upper surface of the spout 150 to prevent water entering the spout 150 from the water tank 140.

The upper wall 146 of the water tank 140 comprises one or more supports 154 for supporting the inverted water tank 140 on a work surface, counter top or other support surface. In this example, two parallel supports 154 are formed in the periphery of the upper wall 146 for supporting the inverted water tank 140.

With reference now to FIGS. 9 to 11 and FIGS. 14 to 16, the base 70 comprises a water reservoir 160 for receiving water from the water tank 140. The water reservoir 160 is a separate component which is inserted between the ends of the supporting wall 84 of the base 70. The water reservoir 160 comprises an inlet chamber 162 for receiving water from the water tank 140, and an outlet chamber 164 for receiving water from the inlet chamber 162, and in which water is atomised to become entrained within the second air flow. The inlet chamber 162 is located on one side of the water reservoir 160, and the outlet chamber 164 is located on the other side of the water reservoir 160.

The water reservoir 160 comprises a base 166 and a side wall 168 extending about and upstanding from the periphery of the base 166. The base 166 is shaped so that the depth of the outlet chamber 164 is greater than the depth of the inlet chamber 162. The sections of the base 166 located within each chamber 162, 164 are preferably substantially parallel, and are preferably parallel to the bottom wall 80 of the base 70 so that these sections of the base 166 are substantially horizontal when the humidifying apparatus 10 is located on a horizontal support surface. The connector 116 for receiving one end of the flexible tube 114 of the inlet duct is connected to, and preferably integral with, the side wall 168 of the water reservoir 160. During assembly, the water reservoir 160 is connected to the base 70 so that the upper end of the connector 116 is aligned with, and abuts, the lower end of the first section 110 of the inlet duct.

The water reservoir 160 is separated into the inlet chamber 162 and the outlet chamber 164 by a dividing wall 170 which extends partially across the water reservoir 160 from the inner periphery of the side wall 168. An aperture 172 located between the end of the dividing wall 170 and the side wall 166 allows water to pass from the inlet chamber 162 to the outlet chamber 164.

The dividing wall 170 defines in part the second manifold 122. The outlet port 124 is formed in the dividing wall 170 so as to emit part of the second air flow into the outlet chamber 164. The manifold 118 is located on the opposite side of the outlet chamber 164 to the manifold 122, and is connected to, and preferably integral with, the side wall 166. The outlet port 120 is formed in the side wall 166 so as to emit at least part of the second air flow into the outlet chamber 164; where the second manifold 122 is not connected to the manifold 118 then the outlet port 120 will emit all of the second air flow into the outlet chamber 164, but otherwise each outlet port 120, 124 will emit part of the second air flow into the outlet chamber 164. Each outlet port 120, 124 lie in a respective plane P1, P2. Each plane P1, P2 is substantially perpendicular to the section of the base 166 defining the outlet chamber 164. The planes P1, P2 are arranged so that the plane P1 is inclined at an acute angle to plane P2. In this embodiment, the angle α subtended between the planes P1, P2 is in the range from 30 to 70°. The outlet ports 120, 124 have substantially the same shape, and are located at the same vertical distance from the section of the base 166 defining the outlet chamber 164.

Figure 14A:
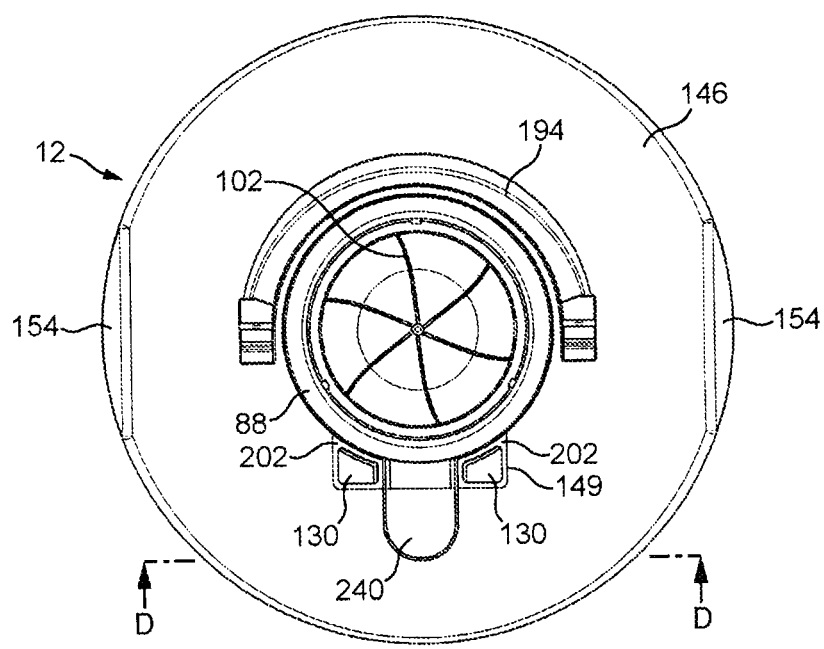
FIG. 14(*a*) is top view of the water tank mounted on the base, and FIG. 14(*b*) is a front sectional view taken along line D-D in FIG. 14(*a*)
Figure 14B:
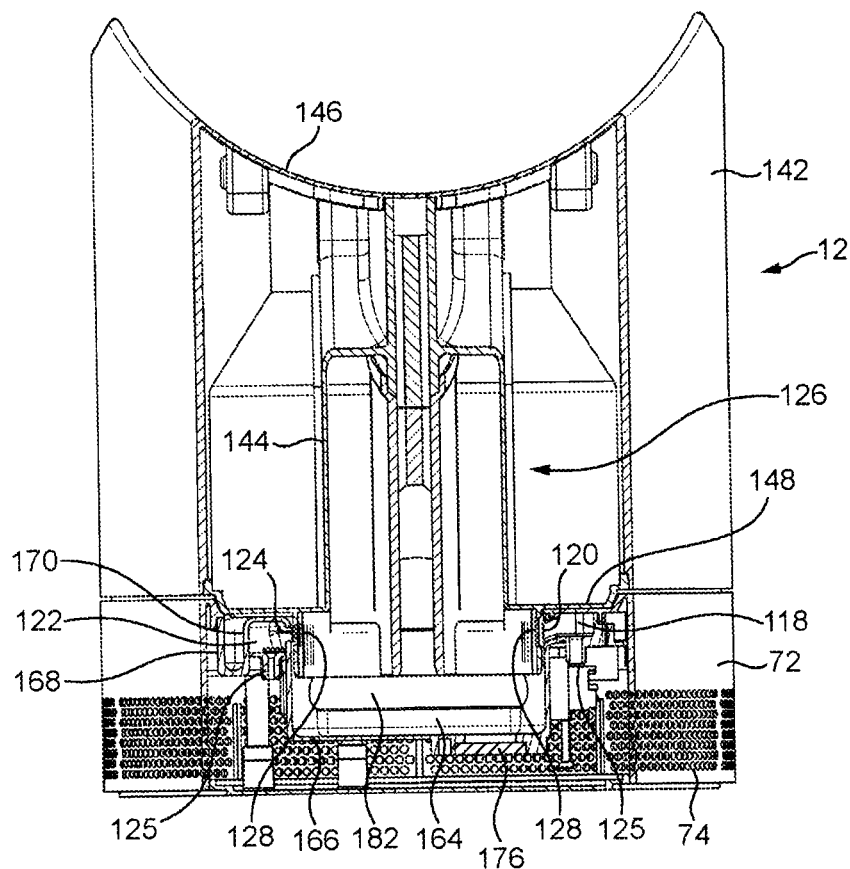
Figure 15:
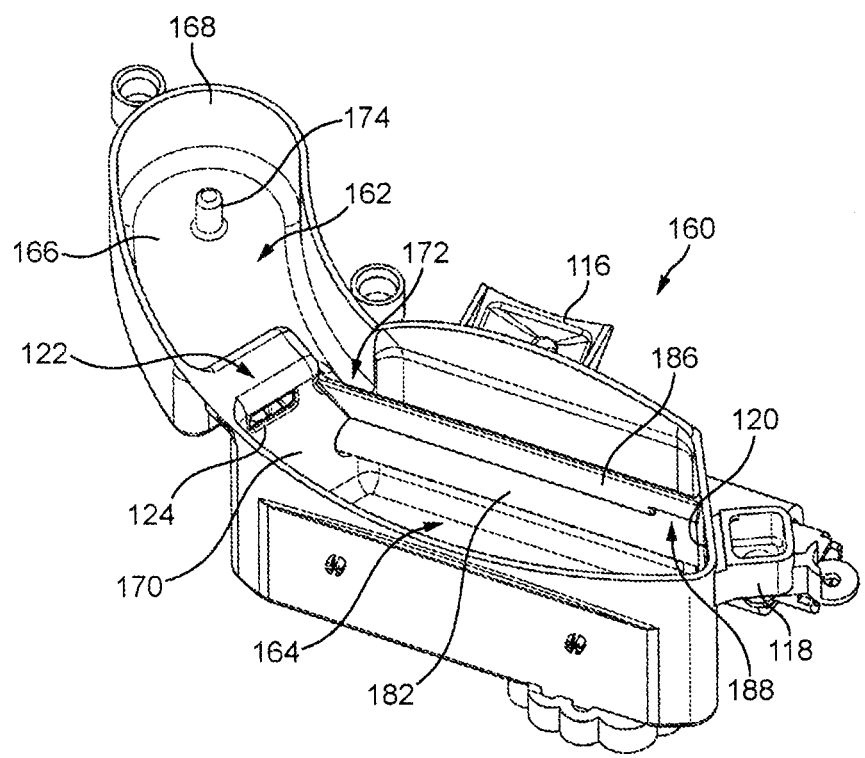
FIG. 15 is a perspective view of a water reservoir of the base.
Figure 16A:
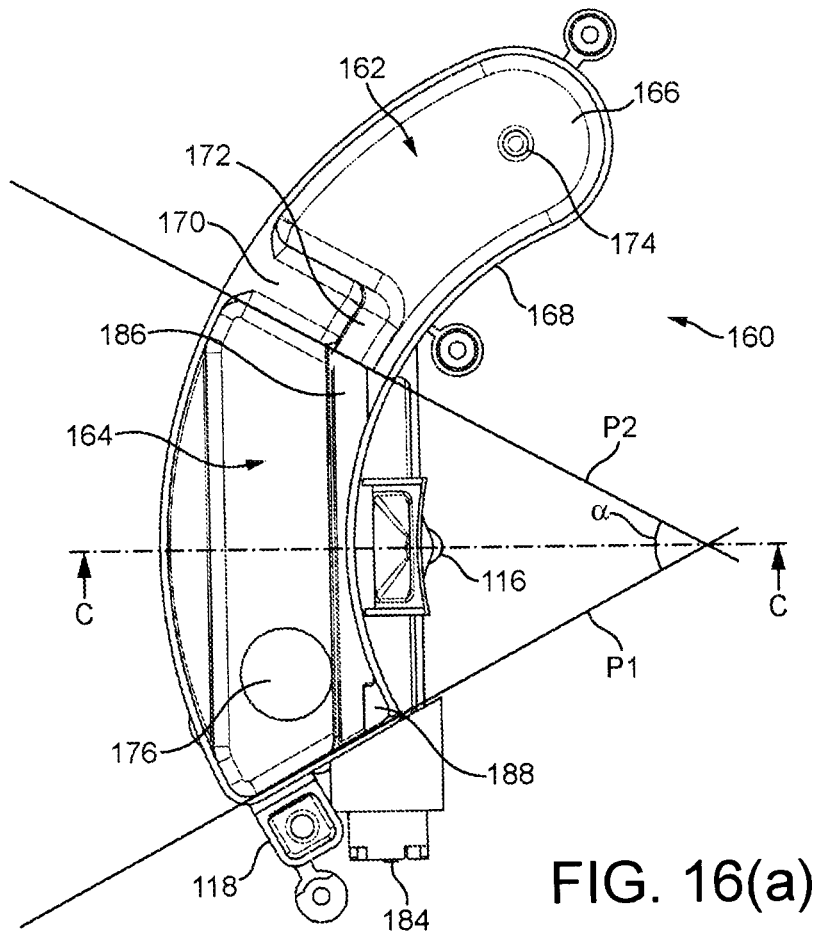
FIG. 16(*a*) is a top view of the water reservoir, and FIG. 16(*b*) is a side sectional view taken along line C-C in FIG. 16(*a*)
Figure 16B:
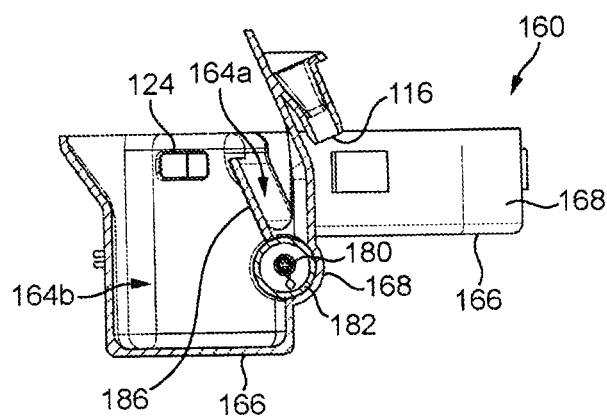

With reference to FIGS. 14(a) and 14(b), when the water tank 140 is mounted on the base 70 the lower portion of the outlet duct 126 extends into the outlet chamber 164. The lower portion of the outlet duct 126 is shaped so that each inlet ports 128 of the outlet duct 126 is aligned with a respective outlet port 120, 124 of the inlet duct so that air emitted from each outlet port 120, 124 passes immediately through a respective inlet port 128 of the outlet duct 126 to enter the outlet duct 126.

Returning to FIGS. 15 and 16, a pin 174 extends upwardly from the section of the base 166 defining the inlet chamber 162. When the water tank 140 is mounted on the base 70, the pin 174 protrudes into the spout 150 to push the valve 152 upwardly to open the spout 150, thereby allowing water to pass under gravity into the inlet chamber 162. As the inlet chamber 162 fills with water, water passes through the aperture 172 to enter the outlet chamber 164. As water is output from the water tank 140, it is replaced within the water tank 140 by air which enters the water tank 140 through a slot 175 located in the side wall of the spout 150. As the chambers 162, 164 fill with water, the level of water within the chambers 162, 164 equalizes. The spout 150 is arranged so that the water reservoir 160 can be filled with water to a maximum level which is substantially co-planar with the upper end of the slot 175 located within the side wall of the spout 150; above that level no air can enter the water tank 140 to replace water output from the water tank 140. This maximum water level is preferably selected so that at least part of each outlet port 120, 124 of the inlet duct lies above this maximum water level. As a result, the second air flow enters the water reservoir 160 directly over the surface of the water located in the outlet chamber 164 of the water reservoir 160.

The section of the base 166 defining the outlet chamber 164 comprises a circular aperture for exposing a piezoelectric transducer 176. The drive circuit 94 is configured to actuate vibration of the transducer 176 in an atomization mode to atomise water located in the outlet chamber 164. In the atomization mode, the transducer 176 may vibrate ultrasonically at a frequency $f_1$, which may be in the range from 1 to 2 MHz.

The water reservoir 160 also includes an ultraviolet radiation (UV) generator for irradiating water within the water reservoir 160. In this embodiment, the UV generator is arranged to irradiate water within the outlet chamber 164 of the water reservoir 160. The UV generator is in the form of a UV lamp 180 located within a UV transparent tube 182. The tube 182 is in turn located within the outlet chamber 164. The tube 182 may be wholly located within the outlet chamber 164. Preferably, one end of the tube 182 protrudes through an aperture formed in the side wall 168 of the water reservoir 160 to expose one or more electrical connectors 184 that allow electrical connections to be made between the drive circuit 94 and the UV lamp 180. An O-ring sealing member may be provided between the tube 182 and the aperture formed in the side wall 168 to inhibit water leakage through the aperture. The UV generator is positioned within the outlet chamber 164 along a portion of the side wall 168 positioned adjacent to the aperture 172 through which water enters the outlet chamber 164.

The water reservoir 160 comprises a baffle plate 186 for guiding water entering the outlet chamber 164 along the tube 182. The baffle plate 186 extends across the outlet chamber 164 from the dividing wall 170 to the portion of the side wall 166 in which the outlet port 120 is formed, and serves to divide the outlet chamber 164 into an inlet section 164a for receiving water from the inlet chamber 162, and an outlet section 164b within which water is atomized by the transducer 176. The baffle plate 186 is shaped so that the lower edge of the baffle plate 186 engages the tube 182 along the length thereof. The lower edge of the baffle plate 186 thus divides the outer surface of the tube 182 into an upper portion located within the inlet section 164a to one side of the baffle plate 186, and a lower portion located within the outlet section 164b to the other side of the baffle plate 186. The upper portion of the tube 182 delimits a lower surface of the inlet section 164a of the outlet chamber 164, and the lower portion of the tube 182 delimits part of a side surface of the outlet section 164b of the outlet chamber 164. As water enters the outlet chamber 164, it is guided by the baffle plate 186 to flow along the inlet section 164a, adjacent the upper portion of the tube 182. A notch formed in the lower edge of the baffle plate 186 defines with the tube 182 an aperture 188 through which water flows from the inlet section 164a to the outlet section 164b.

The upper edge of the baffle plate 186 is located above the maximum water level of the water reservoir 160 A level sensor 190 (illustrated schematically in FIG. 22) is located within the water reservoir 160 for detecting the level of water within the water reservoir 160. The base 70 may also include a proximity sensor 192 for detecting that the water tank 140 has been mounted on the base 70. The proximity sensor 192 may be in the form of a reed switch which interacts with a magnet (not shown) located on the lower wall 148 of the water tank 140 to detect the presence, or absence, of the water tank 140 on the base 70.

Figure 12:
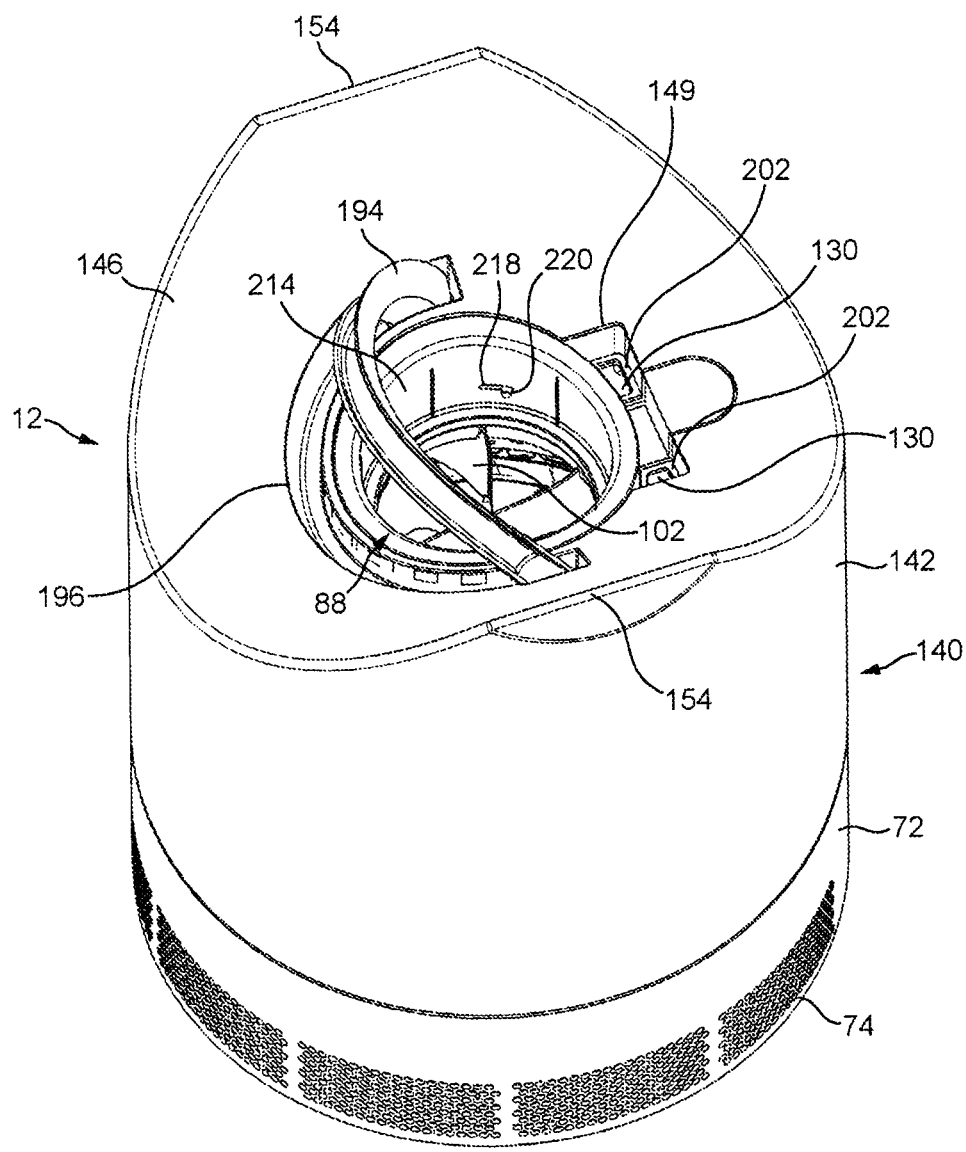
Figure 13A:
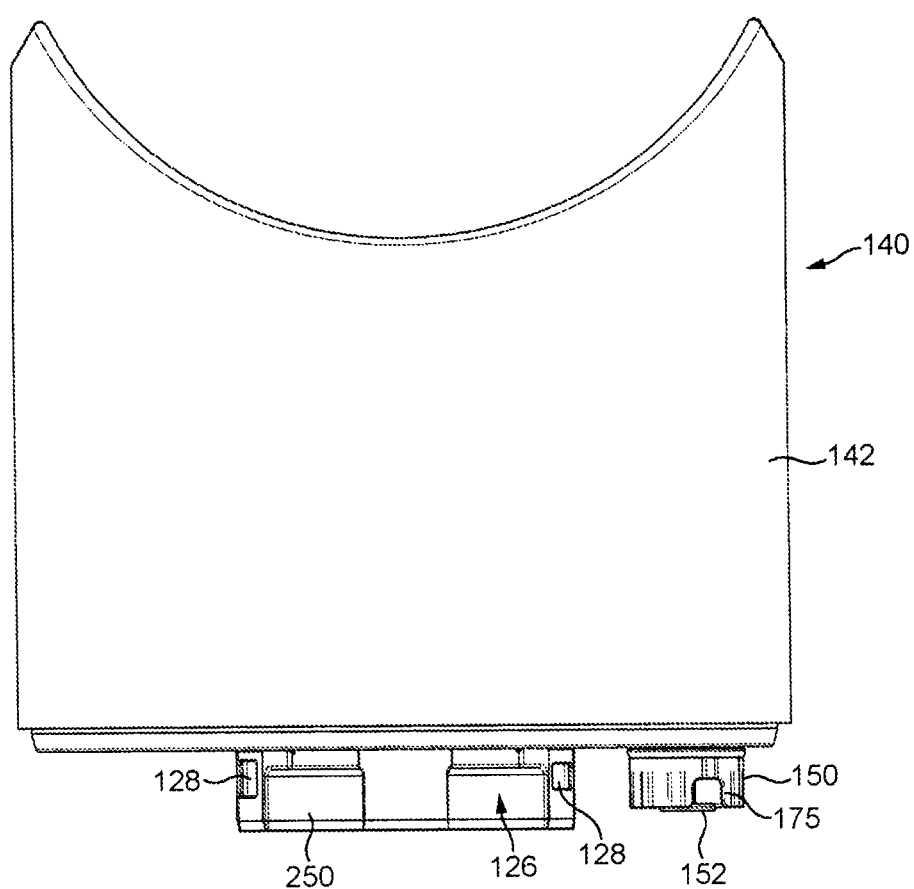
FIG. 13(*a*) is a rear view of the water tank, FIG. 13(*b*) is a top view of the water tank and FIG. 13(*c*) is a bottom view of the water tank.
Figure 13B:
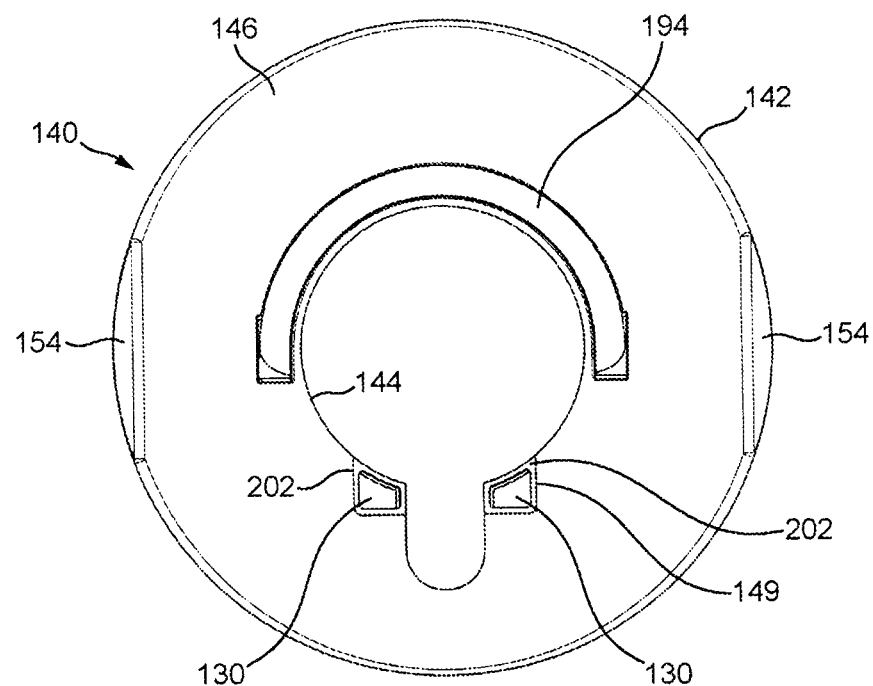
Figure 13C:
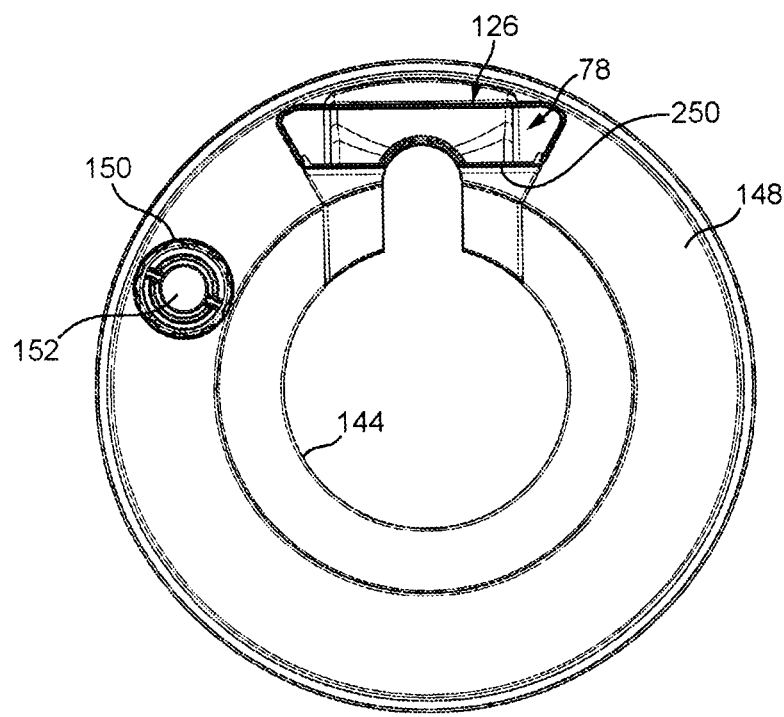

As illustrated in FIG. 12, when the water tank 140 is mounted on the base 70 the inner wall 144 surrounds the upper wall of the base 70 to expose the open upper end of the upper cylindrical section 88 of the upper wall. The water tank 140 includes a handle 194 to facilitate removal of the water tank 140 from the base 70. The handle 194 is pivotably connected to the water tank 140 so as to be moveable relative to the water tank 140 between a stowed position, in which the handle 194 is housed within a recessed section 196 of the upper wall 146 of the water tank 140, and a deployed position, in which the handle 194 is raised above the upper wall 146 of the water tank 140. One or more resilient elements, such as torsion springs, may be provided in the recessed section 196 of the upper wall 146 for biasing the handle 194 towards its deployed position, as illustrated in FIG. 12.

Figure 17:
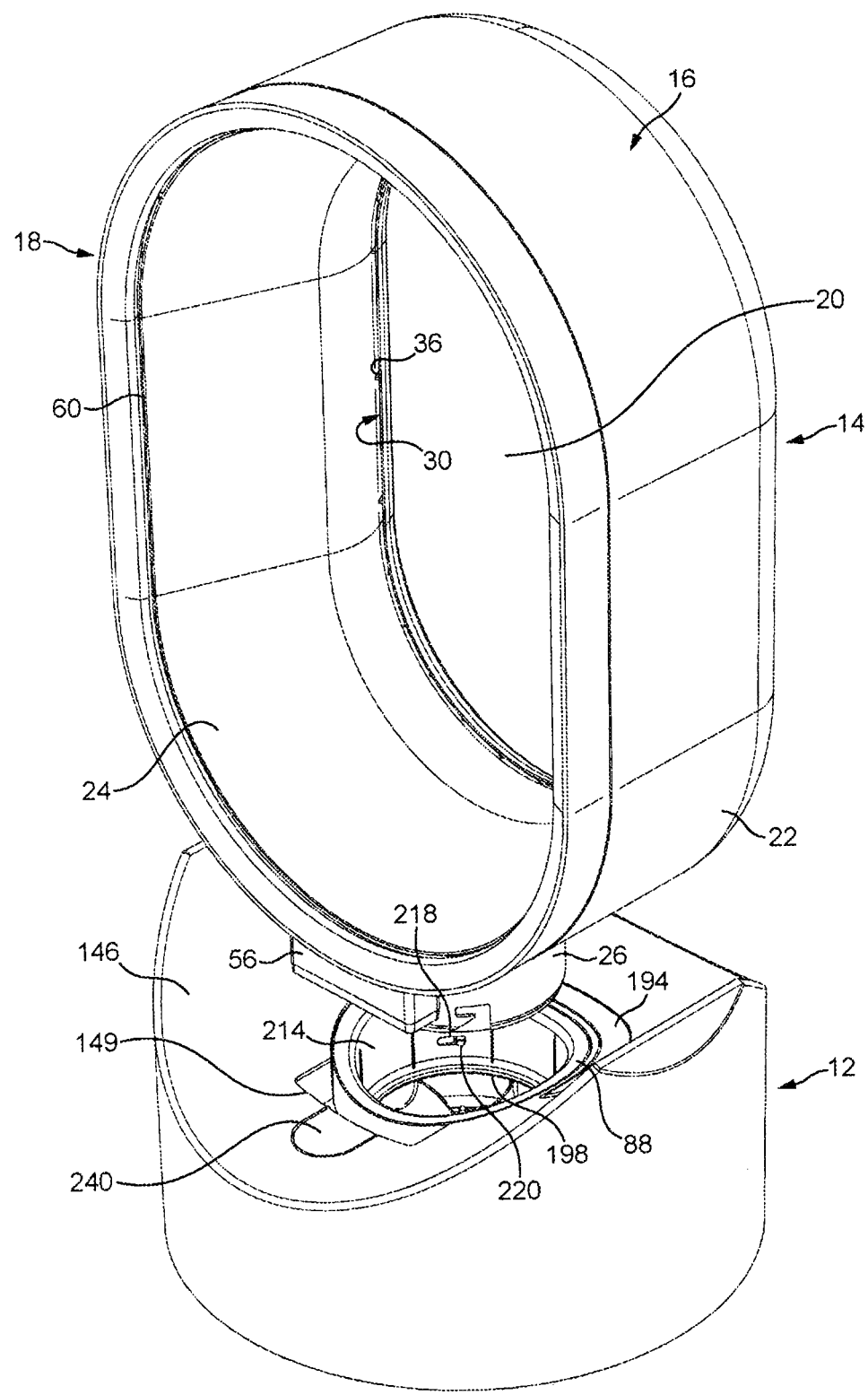
FIG. 17 is a front perspective view of an upper part of the humidifying apparatus, with the nozzle of the humidifying apparatus detached from the body.
Figure 20:
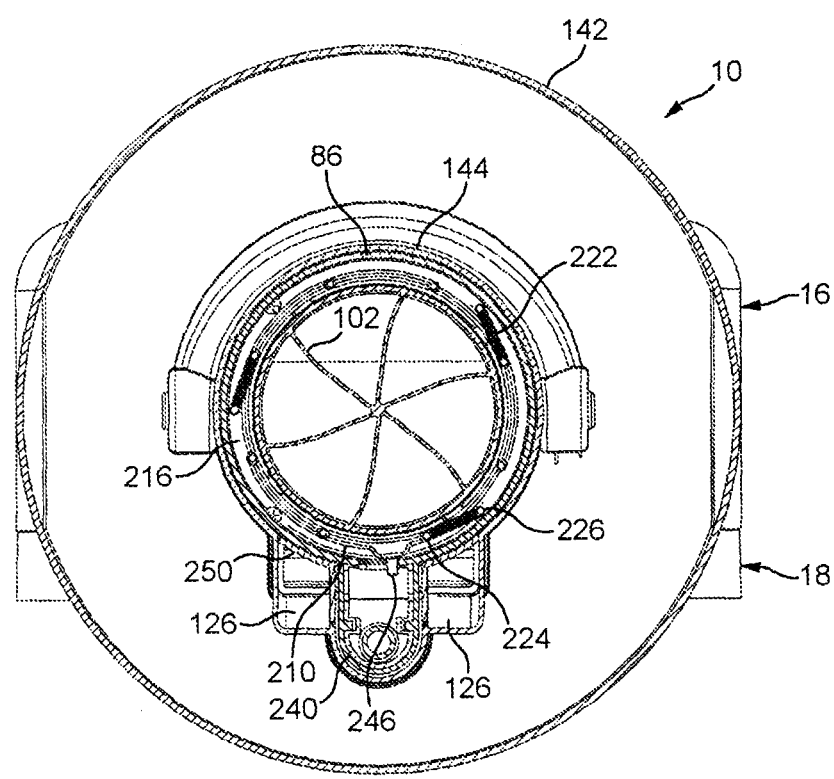
FIG. 20 is a bottom sectional view taken along line H-H in FIG. 4.

With reference to FIG. 17, when the nozzle 14 is mounted on the body 12, the base 26 of the outer casing section 22 of the nozzle 14 is located over the open end of the upper cylindrical section 88 of the upper wall of the base 70, and the base 56 of the front casing section 50 of the nozzle 14 is located over the recessed portion 149 of the upper wall 146 of the water tank 140. The user then pushes the nozzle 14 towards the body 12 so that the base 26 enters the upper cylindrical section 88 of the upper wall of the base 70. Simultaneously, the lower external surface of the outer casing section 22 pushes the handle 194 towards its stowed position, against the biasing force of the resilient elements. A protrusion may be provided on the lower external surface of the outer casing section 22 to engage the handle 194 as the nozzle 14 is pushed on to the body 12.

When the bases 26, 56 of the nozzle 14 are fully inserted in the body 12, a first annular sealing member 198 forms an air tight seal between the lower end of the base 26 and an annular ledge 200 extending radially inwardly from the cylindrical section 88 of the upper wall of the base 70. Second sealing members 202 located within the recessed section 149 of the upper wall 146 of the water tank 140 198 form air tight seals between the lower end of the base 56 and the periphery of the outlet ports 130. The upper wall 146 of the water tank 140 has a concave shape so that, when the nozzle 14 is mounted on the body 12, the water tank 140 surrounds a lower part of the nozzle 14. This not only can this allow the capacity of the water tank 140 to be increased, but can also provide the humidifying apparatus 10 with a compact appearance.

A mechanism is provided for releasably retaining the nozzle 14 on the body 12. With reference to FIGS. 17 to 21, in this embodiment the base 70 of the body 12 comprises the mechanism for releasably retaining the nozzle 14 on the body 12. The mechanism for releasably retaining the nozzle 14 on the body 12 comprises a hoop 210 located within a cavity 212 defined by the cylindrical section 88 of the upper wall of the base 70. The cavity 212 is located between an inner section 214 and an outer section 216 of the cylindrical section 88 of the upper wall of the base 70. The inner section 214 comprises a plurality of angularly spaced, co-planar slots 218. In this embodiment, the inner section 214 comprises three slots 218. The hoop 210 comprises a plurality of detents 220 extending radially inwardly from the inner surface of the hoop 210. Each detent 220 protrudes through a respective one of the slots 218. The hoop 210 is rotatable within the cavity 212 to enable the detents 220 to move along the slots 218. Each detent 220 is moveable between a first, retaining position for retaining the nozzle 14 on the body 12, and a second, release position for allowing the nozzle 14 to be removed from the body 12. Resilient elements are provided for biasing the detents 220 towards their retaining positions. In this example, the resilient elements are in the form of helical tension springs 222. Each spring 222 has one end connected to a respective pin 224 depending downwardly from the lower end of the hoop 210, and the other end connected to a respective pin 226 depending downwardly from the outer section 216 of the cylindrical section 88 of the upper wall of the base 70.

The outer surface of the base 26 of the nozzle 14 comprises a plurality of recesses 228 each for receiving the distal end of a respective detent 220. Each recess 228 is shaped so as to have a lower, open end 230, an upper, closed end 232, a first side wall having an inclined section 234 extending from the lower end 230 and a horizontal section 236 extending from the inclined section 234 to the closed end 232, and a second, generally vertical second side wall 238 opposite to the first side wall.

As the nozzle 14 is mounted on the body 12, each detent 220 engages the lower end of the inclined section 234 of the side wall of a respective recess 228. With further depression of the nozzle 14 on to the body 12, the force applied to the detents 220 by the side walls of the recesses 228 causes the hoop 210 to rotate relative to the nozzle 14, against the biasing force applied thereto by the springs 222, to allow the detents 220 to move from their retaining positions along the inclined sections 234 of the recesses 228. As the detents 220 reach the upper ends of the inclined sections 234 of the recesses 228, the force applied to the detents 220 by the side wall of the recesses 228 is removed. The springs 222 relax, and urge the hoop 210 to rotate within the cavity 212 to return the detents 220 rapidly to their retaining positions. The detents 220 thus become located at the closed ends 232 of the recesses 228. The biasing force applied to the hoop 210 by the springs 222 keeps the detents 220 in their retained positions. In the event that a user should attempt to lift the humidifying apparatus 10 by grasping the nozzle 14 and pulling the nozzle 14 upwards, the engagement of the detents 220 with the horizontal sections 236 of the recesses 228 prevents the nozzle 14 from becoming detached from the body 12.

The body 12 comprises a depressible button 240 for moving the detents 220 from their retaining positions to their release positions to allow the nozzle 14 to be removed from the body 12. In this example, the button 240 is located on the base 70, and is moveable within a housing 242 defined by the upper wall of the base 70. The water tank 140 is shaped so that the upper surface of the button 240 is substantially flush with the upper wall 146 of the water tank 140 when the water tank 140 is mounted on the base 70 and the button 240 is in the raised position.

A notch having an inclined surface 244 is formed on the lower end of the button 240. A finger 246 provided on the outer surface of the hoop 210 extends into the notch so that the finger 246 engages the lower end of the inclined surface 244 of the notch. Depression of the button 240 by the user causes the inclined surface 244 of the notch to apply a force to the finger 246, which in turn causes the hoop 210 to rotate relative to the nozzle 14, against the biasing force applied thereto by the springs 222. This rotation of the hoop 210 moves the detents 220 along the horizontal sections 236 of the recesses 228 from their retaining positions to their release positions, in which the detents 220 are located adjacent the second side walls 238 of the recesses 228. While the detents 220 are maintained in their release positions, through the depression of the button 240 by the user, the user may pull the nozzle 14 from the body 12. With this relative movement between the nozzle 14 and the body 12, the second side walls 238 of the recesses 228 slide along the detents 220 to disengage the detents 220 from the recesses 228, and so release the nozzle 14 from the body 12. Once the nozzle 14 has been lifted from the body 12, the button 240 may be released by the user. The springs 222 urge the hoop 210 to rotate within the cavity 212 to move the detents 220 back to their retaining positions. An additional spring may be located beneath the button 240 to urge the button 240 back to its raised position.

As the nozzle 14 is lifted from the body 12, the resilient element within the water tank 140 urges the handle 194 to its deployed position. The user can then use the handle 194 to lift the water tank 140 from the base 70 to allow the water tank 140 to be filled or cleaned as required. One or more sections of the water tank 140 are preferably removable to facilitate cleaning of the water tank 140. For example, a section 250 of the outlet duct 126 may be removed from the water tank 140 to allow the internal surfaces of the outlet duct 126 to be cleaned. While the nozzle 14 is removed from the body, 12, the user may clean the internal surfaces of the second interior passage 68 of the nozzle 14 by pulling the front section 50 of the nozzle 14 from the inner casing section 24 of the nozzle 14 to expose the internal surfaces of the second interior passage 68. Once the water tank 140 has been filled or cleaned, the user replaces the water tank 140 on the base 70, and then replaces the nozzle 14 on the body 12.

Figure 22:
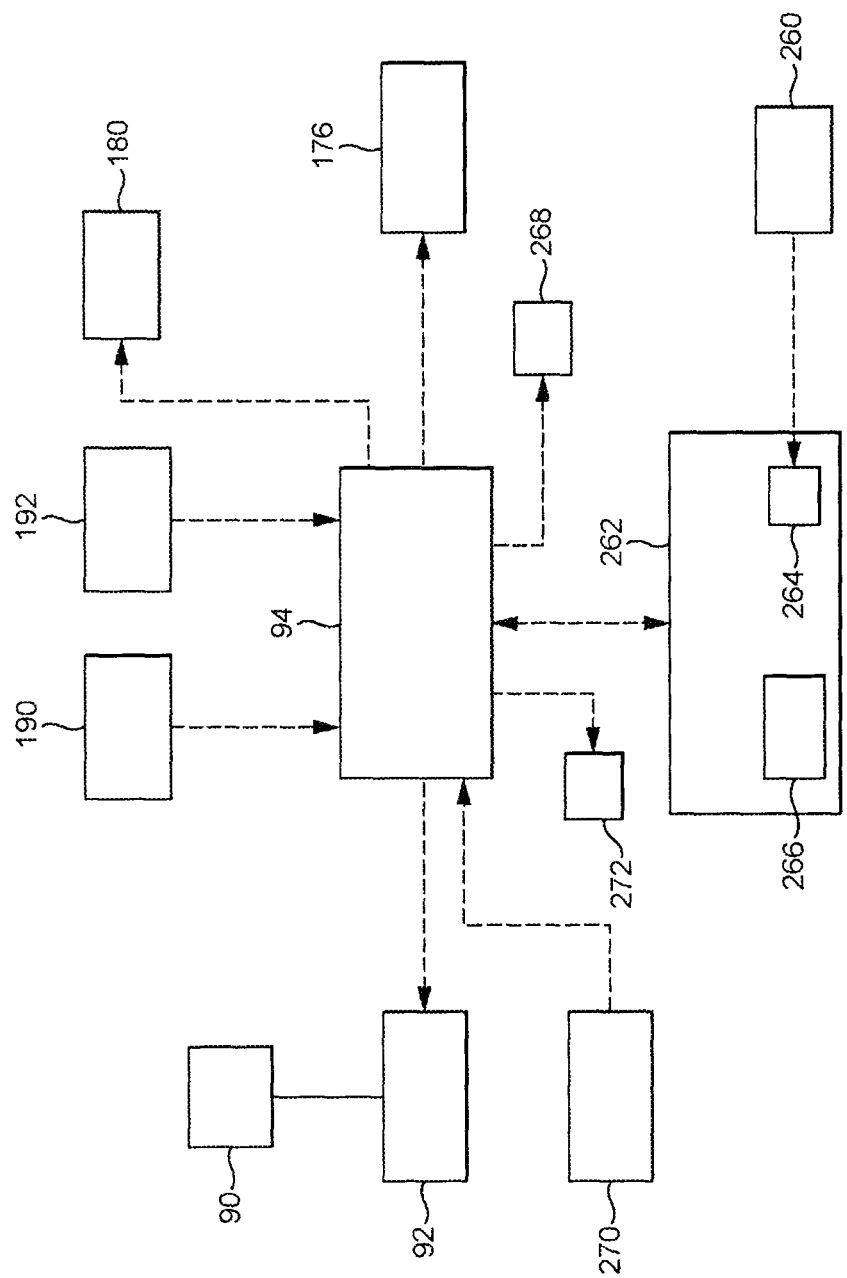
FIG. 22 is a schematic illustration of a control system of the humidifying apparatus.

A user interface (not shown) for controlling the operation of the humidifying apparatus may be located on the outer wall 72 of the base 70 of the body 12. Alternatively, or additionally, the humidifying apparatus 10 may comprise a remote control 260 for transmitting control signals to a user interface circuit 262 of the humidifying apparatus 10. FIG. 22 illustrates schematically a control system for the humidifying apparatus 10, which includes the remote control 260, the user interface circuit 262 and other electrical components of the humidifying apparatus 10. In overview, the remote control 260 comprises a plurality of buttons which are depressible by the user, and a control unit for generating and transmitting infrared light signals in response to depression of one of the buttons. The infrared light signals are emitted from a window located at one end of the remote control 260. The control unit is powered by a battery located within a battery housing of the remote control 260.

A first button is used to activate and deactivate the motor 92, and a second button is used to set the speed of the motor 92, and thus the rotational speed of the impeller 90. The control system may have a discrete number of user selectable speed settings, each corresponding to a respective different rotational speed of the motor 92. A third button is used to set a desired level for the relative humidity of the environment in which the humidifying apparatus 10 is located, such as a room, office or other domestic environment. For example, the desired relative humidity level may be selected within a range from 30 to 80% at 20° C. through repeated actuation of the third button.

The user interface circuit 262 comprises a sensor or receiver 264 for receiving signals transmitted by the remote control 260, and a display 266 for displaying a current operational setting of the humidifying apparatus 10. For example, the display 266 may normally indicate the currently selected relative humidity level. As the user changes the rotational speed of the motor 92, the display 266 may indicate briefly the currently selected speed setting. The receiver 264 and the display 266 may be located immediately behind a transparent or translucent part of the outer wall 72 of the base 70.

The user interface circuit 262 is connected to the drive circuit 94. The drive circuit 94 comprises a microprocessor and a motor driver for driving the motor 92. A mains power cable (not shown) for supplying electrical power to the humidifying apparatus 10 extends through an aperture formed in the base 70. The cable is connected to a plug. The drive circuit 94 comprises a power supply unit connected to the cable. The user interface may also comprise one or more LEDs for providing a visual alert depending on a status of the humidifying apparatus 10. For example, a first LED 268 may be illuminated to indicate that the water tank 140 has become depleted, as indicated by a signal received by the drive circuit 94 from the level sensor 190.

A humidity sensor 270 is also provided for detecting the relative humidity of air in the external environment, and for supplying a signal indicative of the detected relative humidity to the drive circuit 94. In this example the humidity sensor 270 may be located immediately behind the air inlet 74 to detect the relative humidity of the air flow drawn into the humidifying apparatus 10. The user interface may comprise a second LED 272 which is illuminated by the drive circuit 94 when an output from the humidity sensor 270 indicates that the relative humidity of the air flow entering the humidifying apparatus 10, $H_D$, is at or above the desired relative humidity level, $H_S$, set by the user.

Figure 23:
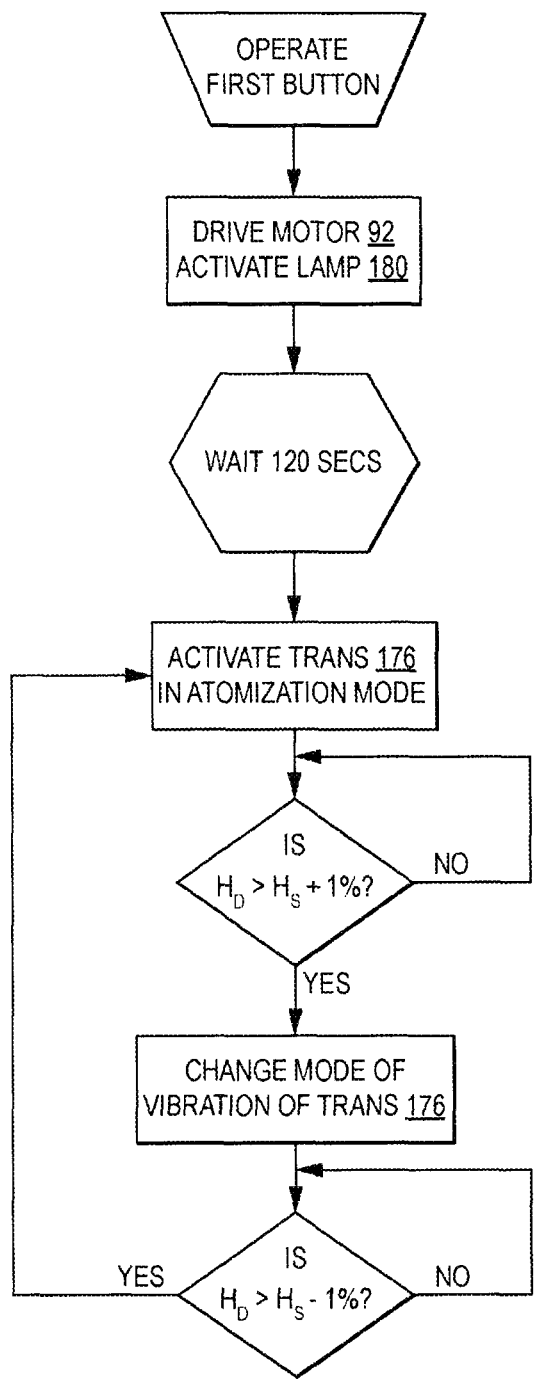
FIG. 23 is a flow diagram illustrating steps in the operation of the humidifying apparatus.

With reference also to FIG. 23, to operate the humidifying apparatus 10, the user actuates the first button of the remote control, in response to which the remote control 260 generates a signal containing data indicative of the actuation of this first button. This signal is received by the receiver 264 of the user interface circuit 262. The operation of the button is communicated by the user interface circuit 262 to the drive circuit 94, in response to which the drive circuit 94 actuates the UV lamp 180 to irradiate water stored in the outlet chamber 164 of the water reservoir 160. In this example, the drive circuit 94 simultaneously activates the motor 92 to rotate the impeller 90. The rotation of the impeller 90 causes air to be drawn into the body 12 through the air inlet 74. An air flow passes through the impeller housing 104 and the diffuser 100. Downstream from the diffuser 100, a portion of the air emitted from the diffuser 100 enters the inlet duct through the inlet port 112, whereas the remainder of the air emitted from the diffuser 100 is conveyed along the first air passageway 76 to the first air inlet 28 of the nozzle 14. The impeller 90 and the motor 92 may thus be considered to generate a first air flow which is conveyed to the nozzle 14 by the first air passageway 76 and which enters the nozzle 14 through the first air inlet 28.

The first air flow enters the first interior passage 46 at the lower end thereof. The first air flow is divided into two air streams which pass in opposite directions around the bore 20 of the nozzle 14. As the air streams pass through the first interior passage 46, air enters the mouth 48 of the nozzle 14. The air flow rate into the mouth 48 is preferably substantially even about the bore 20 of the nozzle 14. The mouth 48 guides the air flow towards the first air outlet 30 of the nozzle 14, from where it is emitted from the humidifying apparatus 10.

The air flow emitted from the first air outlet 30 causes a secondary air flow to be generated by the entrainment of air from the external environment, specifically from the region around the first air outlet 30 and from around the rear of the nozzle 14. Some of this secondary air flow passes through the bore 20 of the nozzle 14, whereas the remainder of the secondary air flow becomes entrained, in front of the nozzle 14, within the air flow emitted from the first air outlet 30.

As mentioned above, with rotation of the impeller 90 air enters the second air passageway 78 through the inlet port 112 of the inlet duct to form a second air flow. The second air flow passes through the inlet duct and is emitted through the outlet ports 120, 124 over the water stored in the outlet section 164b of the outlet chamber 164. The emission of the second air flow from the outlet ports 120, 124 agitates the water stored in the outlet section 164b of the outlet chamber 164. This generates movement of water in front of the lower portion of the tube 182 of the UV generator, increasing the volume of water which is irradiated by the UV lamp 180 prior to actuation of the transducer 176. The relative inclination of the outlet ports 120, 124 can enable the second air flow to generate a swirling motion of water in the outlet section 164b of the outlet chamber 164 to convey water alongside the lower portion of the tube 182.

In addition to the agitation of the water stored in the outlet chamber 164 by the second air flow, the agitation may also be performed by the vibration of the transducer 176 in an agitation mode which is insufficient to cause atomization of the stored water. Depending, for example on the size and the number of transducers 176, the agitation of the stored water may be performed solely by vibration of the transducer 176 at a reduced second frequency $f_2$, and/or at a reduced amplitude, or with a different duty cycle. In this case, the drive circuit 94 may be configured to actuate the vibration of the transducer 176 in this agitation mode simultaneously with the irradiation of the stored water by the UV lamp 180.

The agitation and irradiation of the stored water continues for a period of time sufficient to reduce the level of bacteria within the outlet chamber 164 of the water reservoir 160 by a desired amount. In this example, the outlet chamber 164 has a maximum capacity of 200 ml, and the agitation and irradiation of the stored water continues for a period of 120 seconds before atomization of the stored water commences. The duration of this period of time may be lengthened or shortened depending on, for example, the degree of agitation of the stored water, the capacity of the outlet chamber 164 of the water reservoir 160, and the intensity of the irradiation of the stored water, and so depending on these variables the duration of this period of time may take any value in the range of 10 to 300 seconds to achieve the desired reduction in the number of bacteria within the stored water.

At the end of this period of time, the drive circuit 94 actuates the vibration of the transducer 176 in the atomization mode to atomize water stored in the outlet section 164b of the outlet chamber 164 of the water reservoir 160. This creates airborne water droplets above the water located within the outlet chamber 164 of the water reservoir 160. In the event that the stored water was agitated previously by vibration of the transducer 176 alone, the motor 92 is also activated at this end of this period of time.

As water within the water reservoir 160 is atomized, the water reservoir 160 is constantly replenished with water received from the water tank 140 via the inlet chamber 162, so that the level of water within the water reservoir 160 remains substantially constant while the level of water within the water tank 140 gradually falls. As water enters the outlet chamber 164 from the inlet chamber 162, it is guided by the baffle plate 186 to flow along the upper portion of the tube 182 so that it is irradiated with ultraviolet radiation emitted from the upper portion of the tube 182 before passing through aperture 188 located between the tube 182 and the baffle plate 186. This water is then further irradiated with ultraviolet radiation emitted from the lower portion of the tube 182 before being atomized by the transducer 176. The direction of the movement of the water within the outlet chamber 164, as generated by the second air flow and/or the vibration of the transducer 176, is preferably such that the water flows from the aperture 188 along the lower portion of the tube 182, and in a direction generally opposite to that in which water flows along the upper portion of the tube 182, before being atomized by the transducer 176.

With rotation of the impeller 90, airborne water droplets become entrained within the second air flow emitted from the outlet ports 120, 124 of the inlet duct. The—now moist—second air flow passes upwardly through the outlet duct 126 of the second air passageway 78 to the second air inlets 58 of the nozzle 14, and enters the second interior passage 68 within the front section 18 of the nozzle 14.

At the base of the second interior passage 68, the second air flow is divided into two air streams which pass in opposite directions around the bore 20 of the nozzle 14. As the air streams pass through the second interior passage 68, each air stream is emitted from the second air outlet 60. The emitted second air flow is conveyed away from the humidifying apparatus 10 within the air flow generated through the emission of the first air flow from the nozzle 14, thereby enabling a humid air current to be experienced rapidly at a distance of several meters from the humidifying apparatus 10.

The moist air flow is emitted from the nozzle 14 until the relative humidity $H_D$ of the air flow entering the humidifying apparatus 10, as detected by the humidity sensor 270, is 1% at 20° C. higher than the relative humidity level $H_S$, selected by the user using the third button of the remote control 260. The emission of the moistened air flow from the nozzle 14 may then be terminated by the drive circuit 94, preferably by changing the mode of vibration of the transducer 176. For example, the frequency of the vibration of the transducer 176 may be reduced to a frequency $f_3$, where $f_1 > f_3 \geq 0$, below which atomization of the stored water is not performed. Alternatively the amplitude of the vibrations of the transducer 176 may be reduced. Optionally, the motor 92 may also be stopped so that no air flow is emitted from the nozzle 14. However, when the humidity sensor 270 is located in close proximity to the motor 92 it is preferred that the motor 92 is operated continually to avoid undesirable humidity fluctuation in the local environment of the humidity sensor 270. Also, it is preferred to continue to operate the motor 92 to continue agitating the water stored in the outlet section 164b of the outlet chamber 164 of the water reservoir 160. Operation of the UV lamp 180 is also continued.

As a result of the termination of the emission of a moist air flow from the humidifying apparatus 10, the relative humidity $H_D$ detected by the humidity sensor 270 will begin to fall. Once the relative humidity of the air of the environment local to the humidity sensor 270 has fallen to 1% at 20° C. below the relative humidity level $H_S$ selected by the user, the drive circuit 94 re-activates the vibration of the transducer 176 in the atomization mode. If the motor 92 has been stopped, the drive circuit 94 simultaneously re-activates the motor 92. As before, the moist air flow is emitted from the nozzle 14 until the relative humidity $H_D$ detected by the humidity sensor 270 is 1% at 20° C. higher than the relative humidity level $H_S$ selected by the user.

This actuation sequence of the transducer 176 (and optionally the motor 92) for maintaining the detected humidity level around the level selected by the user continues until the first button is actuated again, or until a signal is received from the level sensor 190 indicating that the level of water within the water reservoir 160 has fallen below the minimum level. If the first button is actuated, or upon receipt of this signal from the level sensor 190, the drive circuit 94 deactivates the motor 92, the transducer 176 and the UV generator to switch off the humidifying apparatus 10. The drive circuit 94 also deactivates these components of the humidifying apparatus 10 in response to a signal received from the proximity sensor 192 indicating that the water tank 140 has been removed from the base 70.

The invention claimed is:

1. Humidifying apparatus comprising:
   a chamber;
   a water tank for supplying water to the chamber;
   at least one baffle located within the chamber for dividing the chamber into an inlet section and an outlet section, and for guiding water received from the water tank along the inlet section to the outlet section;
   an irradiating device for irradiating water in both the inlet section and the outlet section of the chamber, wherein the inlet section and outlet section of the chamber are partially delimited by the irradiating device and the at least one baffle is arranged to divide the irradiating device into a first portion for irradiating water in the inlet section of the chamber, and a second portion for irradiating water in the outlet section of the chamber;
   an atomizing device for atomizing water stored in the outlet section of the chamber;
   an air flow generating device for generating an air flow over water stored in the outlet section of the chamber; and
   at least one air outlet for emitting the air flow.

2. The humidifying apparatus of claim 1, wherein the first portion is located above the second portion.

3. The humidifying apparatus of claim 1, wherein the first portion is contiguous with the second portion.

4. The humidifying apparatus of claim 1, wherein the irradiating device comprises an ultraviolet radiation transparent section, and wherein said at least one baffle is arranged to engage the transparent section to divide the irradiating device into the first portion and the second portion.

5. The humidifying apparatus of claim 4, wherein the transparent section of the irradiating device is convex in shape.

6. The humidifying apparatus of claim 4, wherein the transparent section of the irradiating device is tubular in shape.

7. The humidifying apparatus of claim 6, wherein the transparent section of the irradiating device surrounds an ultraviolet radiation emitting lamp of the irradiating device.

8. The humidifying apparatus of claim 1, wherein the irradiating device is located within the chamber.

9. The humidifying apparatus of claim 1, wherein said at least one baffle is arranged to define, at least in part, an aperture through which water flows from the inlet section to the outlet section.

10. The humidifying apparatus of claim 9, wherein the aperture is located adjacent to the irradiating device.

11. The humidifying apparatus of claim 1, comprising an inlet duct for conveying the air flow towards the outlet section of the chamber, and an outlet duct for conveying the air flow away from the outlet section of the chamber.

12. The humidifying apparatus of claim 11, wherein the inlet duct comprises an outlet port arranged to emit the air flow in such a direction as to generate a movement of the water stored in the outlet section of the chamber.

13. The humidifying apparatus of claim 12, wherein the outlet port of the inlet duct is located in a side wall of the chamber.

14. The humidifying apparatus of claim 12, wherein the outlet port of the inlet duct is arranged to emit air in a direction which is substantially parallel to the upper surface of water stored in the chamber.

15. The humidifying apparatus of claim 11, comprising a base upon which the water tank is mounted, the base comprising the chamber, the air flow generating device and the inlet duct, and the water tank comprising the outlet duct.

16. The humidifying apparatus of claim 15, wherein part of the outlet duct is removable from the water tank.

17. The humidifying apparatus of claim 1, wherein the atomizing device comprises a transducer, and the humidifying apparatus comprises a controller for controlling the irradiating device and the frequency of vibration of the transducer.

18. The humidifying apparatus of claim 1, comprising a nozzle for receiving the air flow, the nozzle comprising said at least one air outlet, the nozzle extending about an opening through which air from outside the apparatus is drawn by air emitted from the nozzle.

* * * * *